(12) United States Patent
Burli et al.

(10) Patent No.: US 7,329,765 B2
(45) Date of Patent: Feb. 12, 2008

(54) BENZOTHIOPHENE COMPOUNDS HAVING ANTIINFECTIVE ACTIVITY

(75) Inventors: Roland W. Burli, San Francisco, CA (US); Eldon E. Baird, Half Moon Bay, CA (US); Matthew J. Taylor, San Francisco, CA (US); Jacob A. Kaizerman, Redwood CitySo. San Francisco, CA (US); Wenhao Hu, San Mateo, CA (US)

(73) Assignee: GeneSoft Pharmaceuticals, Inc., South San Francisco, CA (US)

( * ) Notice: Subject to any disclaimer, the term of this patent is extended or adjusted under 35 U.S.C. 154(b) by 383 days.

(21) Appl. No.: 11/001,237

(22) Filed: Nov. 30, 2004

(65) Prior Publication Data

US 2006/0116326 A1    Jun. 1, 2006

Related U.S. Application Data

(63) Continuation of application No. 10/165,856, filed on Jun. 6, 2002, now Pat. No. 6,825,228.

(60) Provisional application No. 60/325,134, filed on Sep. 24, 2001, provisional application No. 60/298,206, filed on Jun. 13, 2001.

(51) Int. Cl.
| C07D 333/00 | (2006.01) |
| C07D 207/00 | (2006.01) |
| C07D 413/00 | (2006.01) |
| A61K 31/38  | (2006.01) |
| A61K 31/535 | (2006.01) |

(52) U.S. Cl. .................. 549/57; 548/518; 544/111; 514/443; 514/444; 514/422; 514/231.8; 514/236.8

(58) Field of Classification Search ............. 549/57; 548/518; 544/111; 514/443, 444, 422, 231.8, 514/236.8
See application file for complete search history.

(56) References Cited

U.S. PATENT DOCUMENTS

| 3,622,574 | A | 11/1971 | Wright et al. |
| 4,800,211 | A | 1/1989 | Tischler et al. |
| 5,350,748 | A | 9/1994 | Boschelli et al. |
| 5,420,296 | A | 5/1995 | Mongelli et al. |
| 5,472,976 | A | 12/1995 | Animati et al. |
| 5,670,534 | A | 9/1997 | Animati et al. |
| 5,698,674 | A | 12/1997 | Bruice et al. |
| 5,753,629 | A | 5/1998 | Beria et al. |
| 5,801,155 | A | 9/1998 | Kutyavin et al. |
| 5,998,140 | A | 12/1999 | Dervan et al. |
| 6,090,947 | A | 7/2000 | Dervan et al. |
| 6,143,901 | A | 11/2000 | Dervan |
| 6,153,642 | A | 11/2000 | Cozzi et al. |
| 6,172,104 | B1 | 1/2001 | Tidwell et al. |
| 6,177,408 | B1 | 1/2001 | Cozzi et al. |
| 6,458,768 | B1 | 10/2002 | Cozzi et al. |
| 6,482,920 | B1 | 11/2002 | Cozzie et al. |
| 6,545,162 | B1 | 4/2003 | Deryan et al. |
| 6,683,189 | B1 | 1/2004 | Deryan et al. |
| 7,105,564 | B1* | 9/2006 | Honma et al. ............... 514/422 |
| 7,112,594 | B2* | 9/2006 | Ushio et al. ................. 514/324 |
| 7,157,486 | B2* | 1/2007 | Beaulieu et al. ............. 514/415 |
| 2003/0023031 | A1 | 1/2003 | Cozzi et al. |

FOREIGN PATENT DOCUMENTS

| WO | WO98/21202 A1 | 5/1998 |
| WO | WO98/35702 A1 | 8/1998 |

(Continued)

OTHER PUBLICATIONS

Bremer et al., "Recognition of the DNA Minor Groove by Pyrrole-Imidazole Polyamides: Comparison of Desmethyl-and N-Methylpyrrole," *Bioorganic & Medicinal Chemistry*, 8:1947-1955 (2000).

(Continued)

*Primary Examiner*—Rebecca Anderson
*Assistant Examiner*—Joseph R. Kosack
(74) *Attorney, Agent, or Firm*—Townsend and Townsend and Crew LLP

(57) ABSTRACT

Benzothiophene compounds such as are DNA binding compounds exhibiting antibacterial activity.

16 Claims, 10 Drawing Sheets

FOREIGN PATENT DOCUMENTS

| | | |
|---|---|---|
| WO | WO98/37066 A1 | 8/1998 |
| WO | WO98/37067 A1 | 8/1998 |
| WO | WO98/37087 A1 | 8/1998 |
| WO | WO98/45284 A1 | 10/1998 |
| WO | WO98/49142 A1 | 11/1998 |
| WO | WO98/50582 A1 | 11/1998 |
| WO | WO98/52614 A2 | 11/1998 |
| WO | WO99/25686 A1 | 5/1999 |
| WO | WO99/50266 A1 | 10/1999 |
| WO | WO 00/15209 A2 | 3/2000 |
| WO | WO 00/15773 A2 | 3/2000 |
| WO | WO 00/69432 A1 | 11/2000 |
| WO | WO 01/10439 A1 | 2/2001 |
| WO | WO 01/19792 A1 | 3/2001 |
| WO | WO 01/96313 A1 | 12/2001 |
| WO | WO 02/00650 A2 | 1/2002 |

OTHER PUBLICATIONS

Bailly et al., "Sequence-Specific DNA Minor Groove Binders. Design and Synthesis of Netropsin and Distamycin Analogues," *Bioconjugate Chemistry*, 9:513-538 (1998).

White et al., "On the pairing rules for recognition in the minor groove of DNA by pyrrole-imidazole polyamides," *Chemistry & Biology*, 4:569-578 (1997).

Mrksich et al., "Hairpin Peptide Motif. A New Class of Oligopeptides for Sequence-Specific Recognition in the Minor Groove of Double-Helical DNA," *J. Am. Chem. Soc.*, 116:7983-7988 (1994).

Floreancig et al., "Recognition of the Minor Groove of DNA by Hairpin Polyamides Containing α-Substituted-β-Amino Acids," *J. Am. Chem. Soc.*, 122:6342-6350 (2000).

Trauger et al., "Recognition of DNA by designed ligands at subnanomolar concentrations," *Nature*, 382:559-561 (1996).

White et al., "Recognition of the four Watson-Crick base pairs in the DNA minor groove by synthetic ligands," *Nature*, 391:468-471 (1998).

Neidle, Stephen, "DNA minor-groove recognition by small molecules," *Nat. Prod. Rep.*, 18:291-309 (2001).

Fenwick et al., "Solid-Phase Synthesis of Cyclic Alkoxyketones, Inhibitors of the Cysteine Protease Cathepsin K," *Bioorg. Med. Chem. Lett.*, 11:195-198 (2001).

Boger et al., "Total Synthesis of Distamycin A and 2640 Analogues: A Solution-Phase Combinatorial Approach to the Discovery of New Bioactive DNA Binding Agents and Development of a Rapid High-Throughput Screen for Determining Relative DNA Binding Affinity or DNA Binding Sequence Selectivity," 122:6382-6394 (2000).

Boger, D. L. et al., "Paralell Synthesis and Evaluation of 132 (+) - 1,2,9,9a- Tetrahydrocyclopropal [c] benz [e ] indol-4-one (CBI) Analogues of CC-1065 and the Duocarmycins Defining the Contribution of the DNA-Binding Domain, "J. Org. Chem. 2001, vol. 66, pp. 6654-6661.

Baraldi, Pier Giovanni, et al. "Benzoyl and Cinnamoyl Nitrogen Mustard Derivatives of Benzoheterocyclic Analogues of the Tallimustine: Sythesis and Antitumour Activity, "Bioorganic & Medicinal Chemistry, 2002, vol. 10, pp. 1611-1618.

\* cited by examiner (Ib-21)

(Ib-25)

(Ib-22)

(Ib-26)

(Ib-23)

(Ib-27)

(Ib-24)

(Ib-28)

(Ib-29)

(Ib-33)

(Ib-30)

(Ib-34)

(Ib-31)

(Ib-35)

(Ib-32)

(Ib-36)

(Ib-37)

(Ib-41)

(Ib-38)

(Ib-42)

(Ib-39)

(Ib-43)

(Ib-40)

(Ib-44)

(Ib-45)

(Ib-49)

(Ib-46)

(Ib-50)

(Ib-47)

(Ib-51)

(Ib-48)

(Ib-52)

(Ib-53)

(Ib-54)

(Ib-55)

(Ib-56)

(Ib-57)

(Ib-58)

(Ib-59)

(Ib-60)

(Ib-61)

(Ib-62)

(Ib-63)

(Ib-68)

(Ib-64)

(Ib-69)

(Ib-65)

(Ib-70)

(Ib-66)

(Ib-71)

(Ib-67)

(Ib-72)

(Ib-73)

(Ib-78)

(Ib-74)

(Ib-75)

(Ib-76)

(Ib-77)

(Id-1)

(Id-2)

(Id-3)

(Id-4)

(Id-5)

(Ie-1)

(Ie-2)

(Ie-3)

(Ie-4)

BENZOTHIOPHENE COMPOUNDS HAVING ANTIINFECTIVE ACTIVITY

CROSS-REFERENCES TO RELATED APPLICATIONS

This application claims the benefit of U.S. Ser. Nos. 60/325,134, filed Sep. 24, 2001, and 60/298,206, filed Jun. 13, 2001; the disclosures of which are incorporated herein by reference.

STATEMENT AS TO RIGHTS TO INVENTIONS MADE UNDER FEDERALLY SPONSORED RESEARCH OR DEVELOPMENT

This invention was made with Government support under Grant No. N65236-99-1-5427 awarded by the Space and Naval Warfare Systems Command. The Government has certain rights in this invention.

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

1. Field of the Invention

This invention relates to compounds having benzothiophene groups, in particular those binding to nucleic acids and having anti-bacterial properties, and methods for their use.

2. Description of Related Art

A number of naturally occurring or synthetic compounds bind to double stranded nucleic acid, especially double stranded DNA ("dsDNA"). Some bind to the major groove, while others bind to the minor groove. Still others intercalate between adjacent base pairs. Combination binding modes are known, in which a compound has binding interactions with more than one nucleic acid site.

The natural products distamycin and netropsin represent a class of DNA-binding compounds that has been studied over the years:

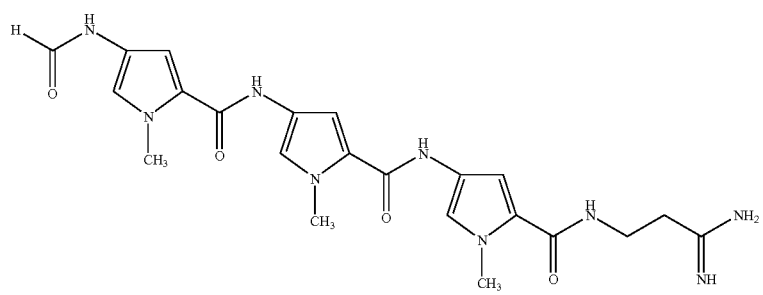

Distamycin

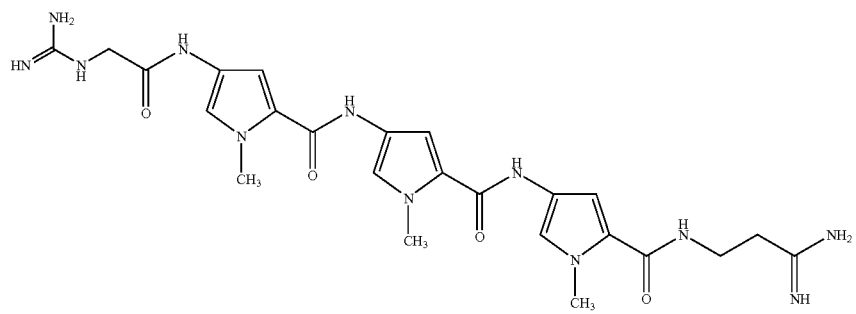

Netropsin

Structurally, distamycin and netropsin are heteroaromatic polyamides, having as their core structural motif N-methylpyrrole carboxamide residues. They bind to the minor groove, their crescent molecular shapes providing a conformational fit within the groove. The binding occurs with a preference for A,T rich dsDNA tracts.

A number of heteroaromatic polyamides have been synthesized elaborating on the distamycin/netropsin motif, with the objective of enhancing or varying biological properties, increasing binding affinity to dsDNA, and/or improving specificity in base pair sequence recognition. The use of synthetic heteroaromatic polyamides in therapeutics has been proposed, for example, in Dervan et al., U.S. Pat. No. 5,998,140 (1999); Dervan et al., WO 00/15209 (2000); Dervan, WO 00/15773 (2000); and Gottesfeld et al., WO 98/35702 (1998).

The effect of structural variations in the heteroaromatic ring has been a focus of extensive research. See, e.g., reviews by Bailly et al., *Bioconjugate Chemistry*, Vol. 9, No. 5, pp. 513–538 (1998) and Neidle, *Nat. Prod. Rep.* 2001, 18, 291–309. Alternative heteroaromatic rings reported in the art include furan, imidazole (especially N-methylimidazole), isoxazole, oxazole, pyrazole, pyridine, thiophene, triazole rings, and others. Art that may be relevant to the use of benzothiophene groups in DNA binding compounds includes Boger et al., *J. Am. Chem. Soc.,* 2000, 122, 6382; Kutyavin et al., U.S. Pat. No. 5,801,155 (1998); Tidwell et al., U.S. Pat. No. 6,172,104 (2001); Cozzi et al., WO 98/21202 (1998); Cozzi et al., WO 99/50266 (1999); and Turin et al., WO 01/19792 (2001).

BRIEF SUMMARY OF THE INVENTION

The present invention provides benzothiophene compounds of the formula

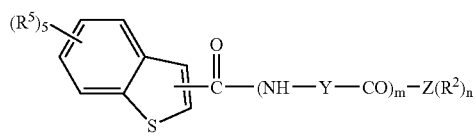

(I)

including the pharmaceutically acceptable salts thereof.

Each $R^5$ is independently H, F, Cl, Br, I, CN, OH, $NH_2$, a substituted or unsubstituted $(C_1-C_{12})$alkyl group, a substituted or unsubstituted $(C_1-C_{12})$alkoxy group, or a substituted or unsubstituted $(C_1-C_{12})$heteroalkyl group. Each $R^2$ is independently H, a substituted or unsubstituted $(C_1-C_{12})$ alkyl group, or a substituted or unsubstituted $(C_1-C_{12})$ heteroalkyl group. Subscript m is an integer from 1 to 25, inclusive. Z is either O or N, with n being 1 if Z is O and 2 if Z is N. Each Y is independently a branched or unbranched, substituted or unsubstituted $(C_1-C_5)$alkylene group or a substituted or unsubstituted, aromatic or heteroaromatic ring system, wherein the ring system can comprise a 5- or 6-member aromatic or heteroaromatic ring or fused 6,6 or 6,5 aromatic or heteroaromatic rings, with the proviso that at least one Y is a substituted or unsubstituted aromatic or heteroaromatic ring system. Preferably, at least one Y is a 5- or 6-member heteroaromatic ring. More preferably, Y in the moiety —(NH—Y—CO)— immediately adjacent to the moiety

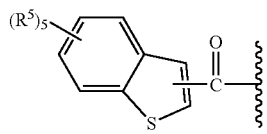

is a 5- or 6-member heteroaromatic ring.

Preferably, each moiety —(NH—Y—CO)— is independently selected from the group consisting of (a) moieties $M^1$ of the formula

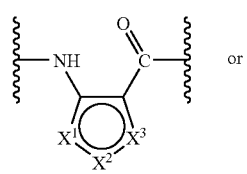

(IIa)

-continued

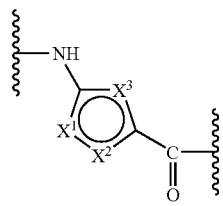

(IIb)

wherein one of $X^1$, $X^2$, and $X^3$ is a ring vertex selected from the group consisting of —O—, —S—, and —$NR^2$—, and the other two of $X^1$, $X^2$, and $X^3$ are ring vertices selected from the group consisting of =N— and =$CR^1$—;

(b) moieties $M^2$ of the formula

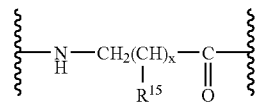

(III)

wherein x is 0 or 1 and each $R^{15}$ is independently H, OH, $NH_2$, or F;

(c) moieties $M^3$ of the formula

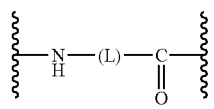

(IV)

wherein each L is independently a divalent moiety separating —NH— and —(C=O)— by 3 or 4 atoms; and (d) moieties $M^4$ of the formula

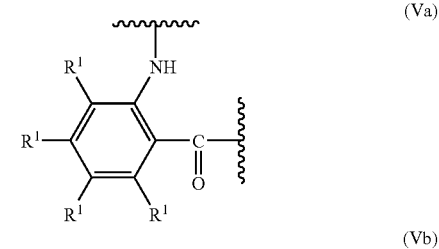

(Va)

(Vb) or

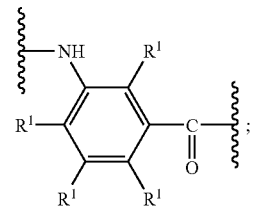

(Vc)

with the proviso that at least one moiety —(NH—Y—CO)— is $M^1$ or $M^4$;

and the compound contains a basic group having a $pK_b$ of 12 or less or a quaternized nitrogen group.

Preferably, at least one moiety —(NH—Y—CO)— is a moiety $M^1$. More preferably, the moiety —(NH—Y—CO)— immediately adjacent to the residue

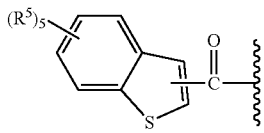

is a moiety $M^1$.

In the preceding formulae $R^1$ and $R^2$ are as previously defined.

Preferably, $R^1$ is hydrogen, halogen (F, Cl, Br, or I, especially F or Cl), a ($C_1$–$C_5$)alkyl group such as methyl, ethyl, propyl, isopropyl, butyl, isobutyl, s-butyl, pentyl, and the like, a ($C_1$–$C_5$)alkoxy group such as methoxy, ethoxy, propoxy, isopropoxy, butoxy, and the like, hydroxy, or cyano. Preferably, each $R^2$ is H or a ($C_1$–$C_5$)alkyl group such as methyl, ethyl, propyl, isopropyl, butyl, isobutyl, s-butyl, pentyl, and the like.

DETAILED DESCRIPTION OF THE INVENTION

Abbreviations and Definitions

Figure 1:
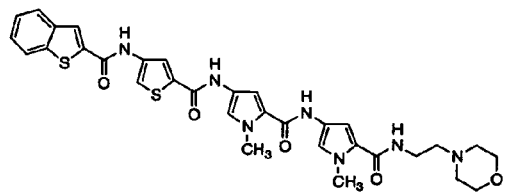
FIGS. 1 through 10 depict compounds of this invention.
Figure 1:
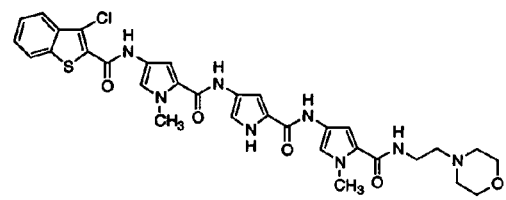
Figure 1:
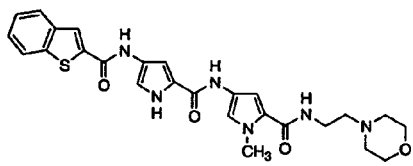
Figure 1:
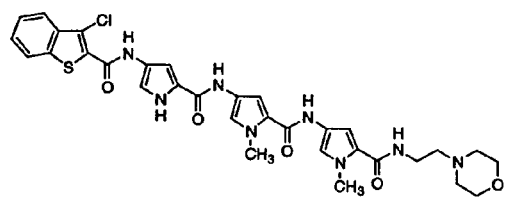
Figure 1:
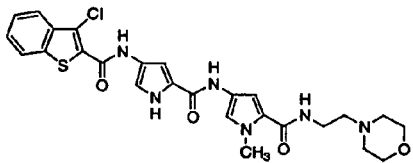
Figure 1:
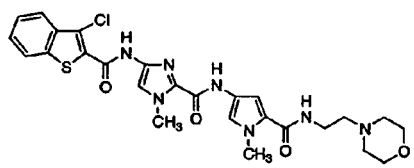
Figure 1:
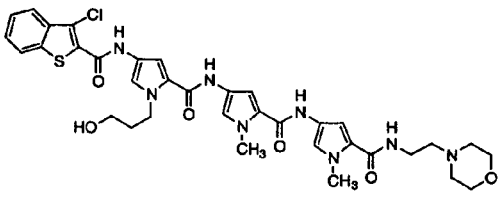
Figure 1:
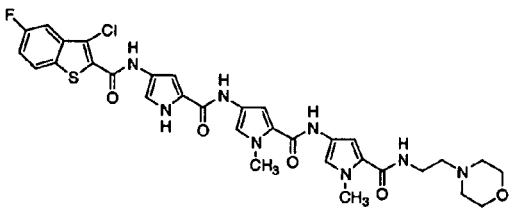
Figure 2:
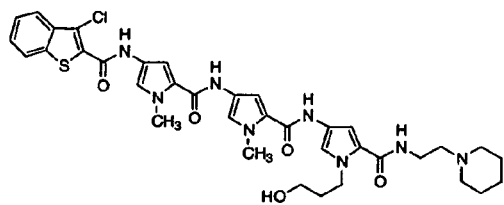
Figure 2:
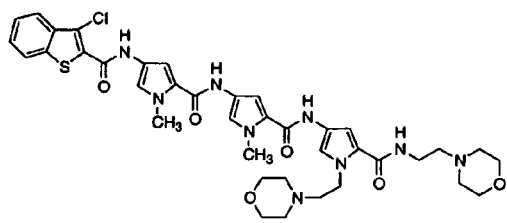
Figure 2:
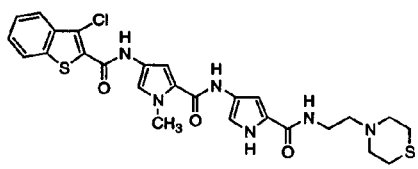
Figure 2:
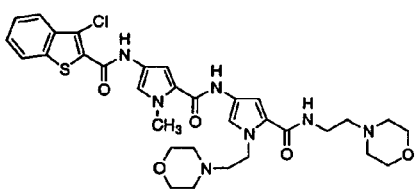
Figure 2:
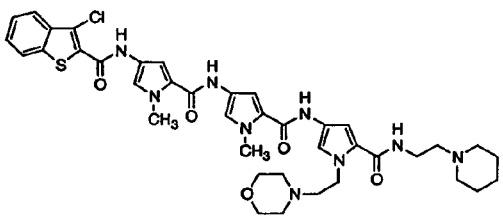
Figure 2:
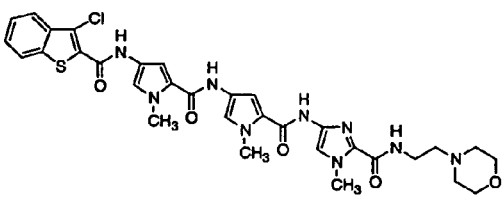
Figure 2:
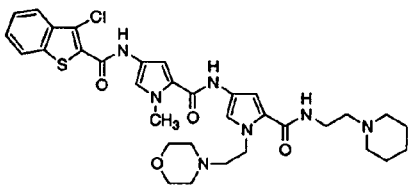
Figure 2:
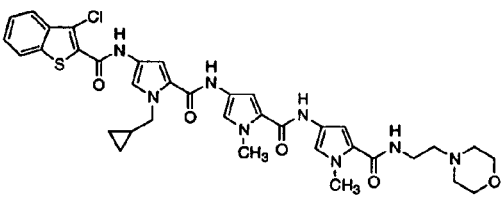
Figure 3:
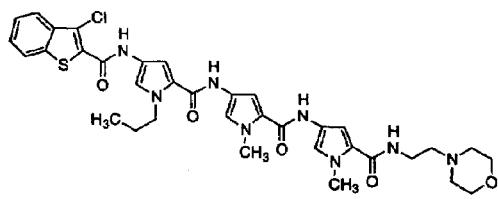
Figure 3:
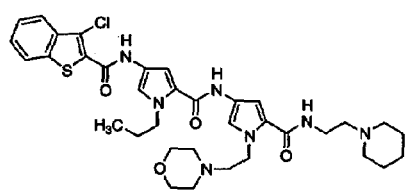
Figure 3:
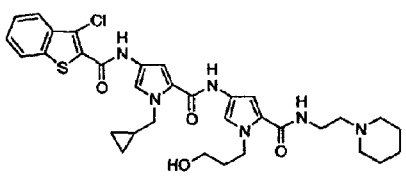
Figure 3:
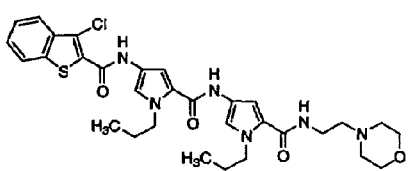
Figure 3:
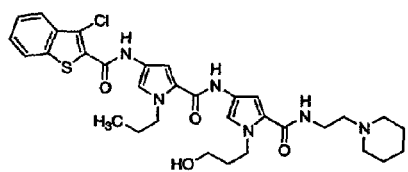
Figure 3:
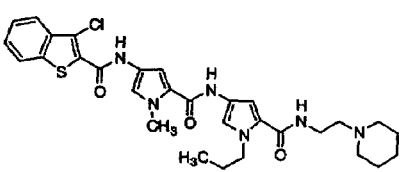
Figure 3:
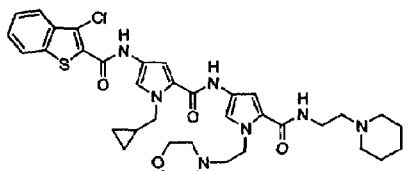
Figure 3:
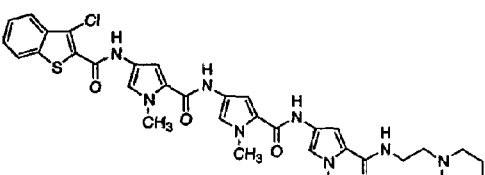
Figure 4:
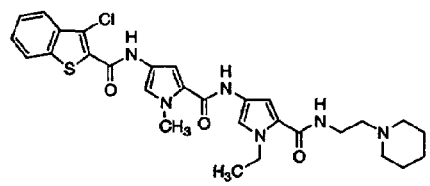
Figure 4:
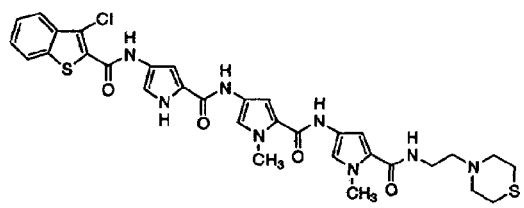
Figure 4:
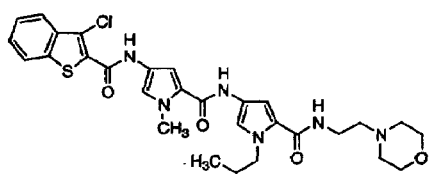
Figure 4:
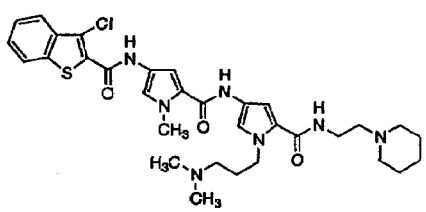
Figure 4:
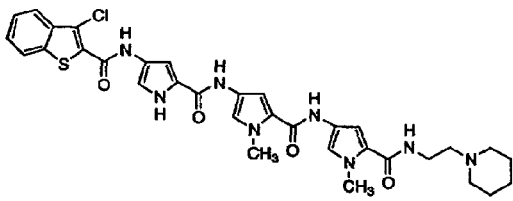
Figure 4:
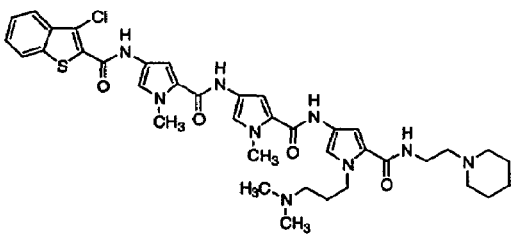
Figure 4:
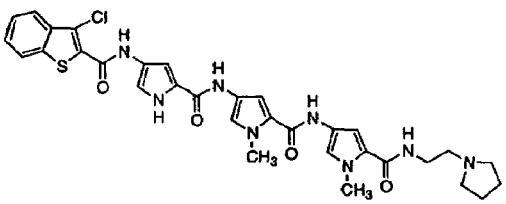
Figure 4:
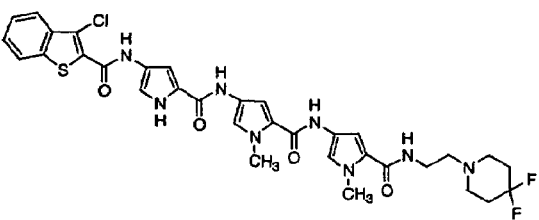

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$–$C_{10}$ means one to ten carbons). Examples of saturated hydrocarbon radicals include groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "alkylene" by itself or as part of another substituent means a divalent radical derived from an alkane, as exemplified by —$CH_2CH_2CH_2CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having six or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified by —$CH_2$—$CH_2$—S—$CH_2CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo ($C_1$–$C_4$)alkyl" is meant to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon substituent, which can be a single ring, or multiple rings (up to three rings), which are fused together or linked covalently. The term "heteroaryl" refers to aryl groups (or rings) that contain from zero to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g. aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") is meant to include both substituted and unsubstituted forms of the indicated radical. Preferred substituents for each type of radical are provided below.

Substituents for the alkyl, heteroalkyl, aryl, and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups selected from: —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —CN and —NO$_2$ in a number ranging from zero to (2m'+1), where m' is the total number of carbon atoms in such radical. R', R" and R''' each independently refer to hydrogen, unsubstituted (C$_1$–C$_8$)alkyl and heteroalkyl, unsubstituted aryl, aryl substituted with 1–3 halogens, unsubstituted alkyl, alkoxy or thioalkoxy groups, or aryl-(C$_1$–C$_4$)alkyl groups. When R' and R" are attached to the same nitrogen atom, they can be combined with the nitrogen atom to form a 5-, 6-, or 7-membered ring. For example, —NR'R" is meant to include 1-pyrrolidinyl and 4-morpholinyl. From the above discussion of substituents, one of skill in the art will understand that the term "alkyl" is meant to include groups such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like). Preferably, the substituted alkyl and heteroalkyl groups have from 1 to 4 substituents, more preferably 1, 2 or 3 substituents. Exceptions are those perhalo alkyl groups (e.g., pentafluoroethyl and the like), which are also preferred and contemplated by the present invention.

Similarly, substituents for the aryl and heteroaryl groups are varied and are selected from: halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R''', —NH—C(NH$_2$)=NH, —NR'C(NH$_2$)=NH, —NH—C(NH$_2$)=NR', —S(O)R', —S(O)$_2$R', —S(O)$_2$NR'R", —N$_3$, —CH(Ph)$_2$, perfluoro(C$_1$–C$_4$)alkoxy, and perfluoro(C$_1$–C$_4$)alkyl, in a number ranging from zero to the total number of open valences on the aromatic ring system; and where R', R" and R''' are independently selected from hydrogen, (C$_1$–C$_8$)alkyl and heteroalkyl, unsubstituted aryl and heteroaryl, (unsubstituted aryl)-(C$_1$–C$_4$)alkyl, and (unsubstituted aryl)oxy-(C$_1$–C$_4$)alkyl.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted (C$_1$–C$_6$)alkyl.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogen-carbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, ascorbic, propionic, isobutyric, maleic, malonic, lactic, malic, glutamic, benzoic, succinic, suberic, fumaric, mandelic, phthalic, benzenesulfonic, ptolylsulfonic, citric, tartaric, methanesulfonic, lactobionic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science*, 1977, 66, 1–19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (chiral centers) or double bonds; the racemates, diastereomers, geometric isomers and individual isomers are all intended to be encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

In the discussions below, reference is made to dsDNA as the nucleic acid, but it is to be understood that the invention is not limited to dsDNA and is applicable to other nucleic acids, i.e., ribonucleic acid.

Compounds

Compounds (I) of this invention are polyamides (or oligoamides) having a benzothiophene carboxamide unit and, additionally, aliphatic, aromatic, and/or heteroaromatic carboxamide units. The compounds are DNA-binding compounds, having an affinity for the minor groove thereof. Different polyamide-dsDNA binding modes are possible. In the simplest mode, often referred to as the 1:1 binding mode, a single polyamide molecule fits in the channel formed by the minor groove. In what is referred to as the 2:1 binding mode, two polyamide molecules fit at the same site in the minor groove, often aligned side-by-side in an antiparallel manner (i.e., with one polyamide being aligned N-to-C and the other polyamide being aligned C-to-N, where "C" and "N" refer to the carboxy and amino termini, respectively of the polyamides). When binding in the 2:1 mode, the compounds may alternatively overlap only partially—the so-called "slipped" binding configuration. Lastly, in what is referred to as a "hairpin" binding mode, a single polyamide molecule that has a more or less centrally positioned flexible moiety (i.e., a moiety $M^3$, as discussed in greater detail here-inbelow) folds around itself to adopt a hairpin conformation when it is bound to the minor groove, so that a first portion of the polyamide at one side of the hairpin turn is adjacent to a second portion of the polyamide at the other side of the hairpin turn.

In formula (I)

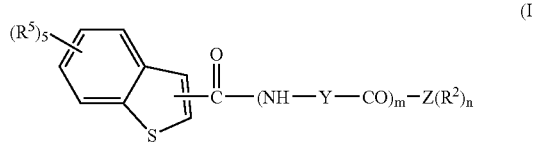

(I)

the benzothiophene group has bonded to each non-bridgehead carbon either a group $R^5$ or the group —C(=O)—(NH—Y—C=O)$_m$-Z(R$^2$)$_n$. Preferably, the latter group is bonded to either the benzothiophene C2 or C3 and the benzothiophene group has a chlorine at position C3 or C2, depending on the positioning of the group —C(=O)—(Y)$_m$-Z(R$^2$)$_n$. That is, the residue

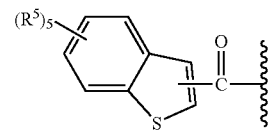

preferably is either

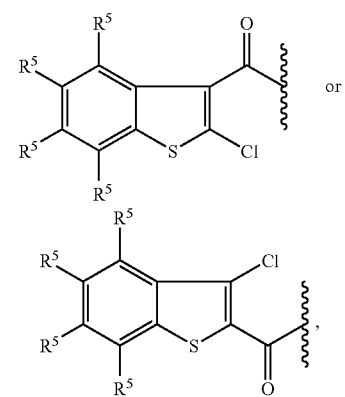

especially where each $R^5$ is H.

In another preferred embodiment, the residue is

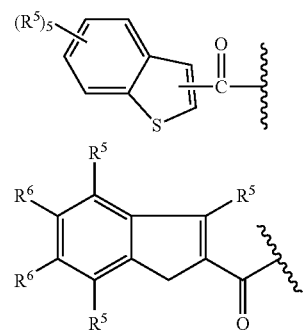

where each $R^5$ is as previously defined and the two $R^6$'s are both OH or OCH$_3$ or combine to form O—(CH(R$^7$))$_t$—O, where t is 1 or 2 and each $R^7$ is independently H or C$_1$–C$_6$ alkyl, alkenyl, alkynyl, or acyl. Specific examples include:

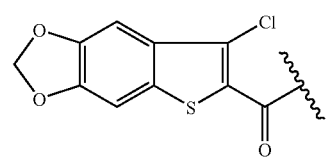

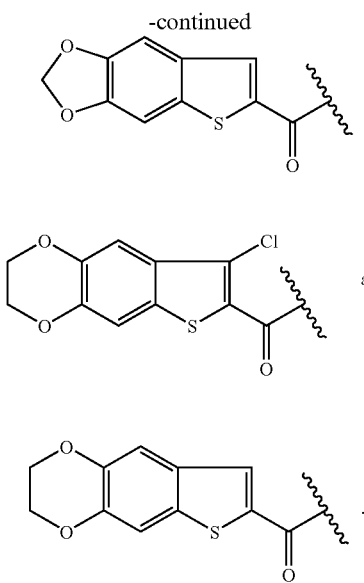

Moieties M¹, described by formulae IIa and IIb

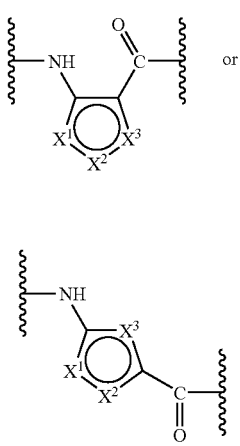

provide additional heteroaromatic polyamide building blocks. Moieties M¹ are 5-membered ring heteroaromatic moieties, the selection of $X^1$, $X^2$, and $X^3$ determining the type of heteroaromatic ring. Exemplary heteroaromatic rings include imidazole, pyrrole, pyrazole, furan, isothiazole, oxazole, isoxazole, thiazole, furazan, 1,2,3-thiadiazole, 1,2,4-thiadiazole, 1,2,5-thiadiazole, 1,3,4-thiadiazole, 1,2,3-triazole, 1,2,4-triazole, 1,3,4-oxadiazole, 1,2,4-oxadiazole, and thiophene. Preferably, at least one moiety (NH—Y—C=O) is a moiety M¹.

The circle in the five-membered rings of formulae IIa and IIb above is meant to indicate the presence of two double bonds, which, in some embodiments, can move within the ring.

Preferred moieties M¹ are IIc (hereinafter "Py"), formally derived from 1-methyl-4-aminopyrrole-2-carboxylic acid, IId (hereinafter "Hp"), formally derived from 1-methyl-3-hydroxy-4-aminopyrrole-2-carboxylic acid, and IIe (hereinafter "Im"), formally derived from 1-methyl-4-aminoimidazole-2 carboxylic acid:

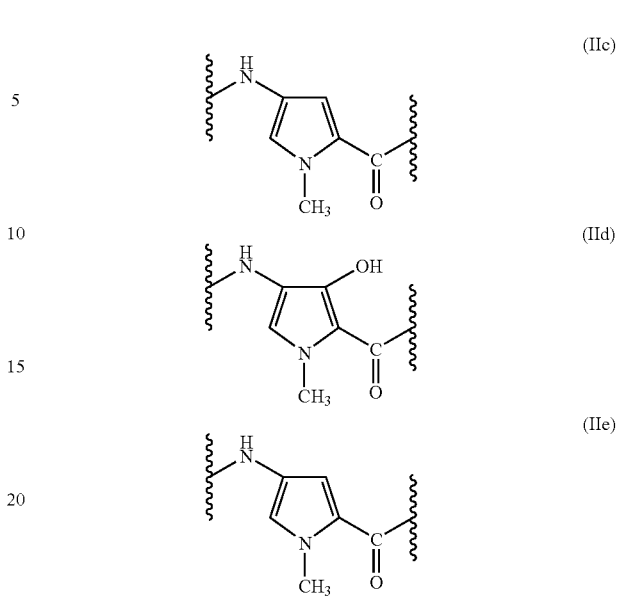

Dervan and co-workers—see, e.g., Dervan, U.S. Pat. No. 6,143,901 (2000); Dervan et al., WO 98/37066 (1998); White et al., Nature 391, 468 (1998); White et al., Chem. Biol. 1997, 4, 569)—have shown that the moieties Py, Im, and Hp can be used to construct a polyamide that, when binding in a 2:1 mode or hairpin configuration, recognizes specific dsDNA base pairs, giving rise to a set of "pairing rules" correlating heteroaromatic moiety pairs and DNA base pairs. These pairing rules are summarized below:

| Heteroaromatic Pair | dsDNA Base Pair(s) Recognized |
| --- | --- |
| Im/Py | G/C |
| Py/Im | C/G |
| Py/Py | A/T, T/A (degenerate) |
| Hp/Py | T/A |
| Py/Hp | A/T |

See, e.g., White et al., Chem. Biol. August 1997, 4, 459 and White et al., Nature 1998, 391, 468. Such recognition ability can lead to sequence-specific dsDNA binding, enabling the design of compounds (I) that target predetermined DNA base pair sequences, for example, a specific promoter site or a sequence characteristic of a gene.

Optionally, compound (I) can include one or more moieties M²

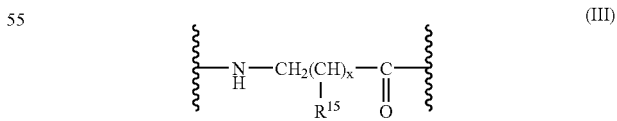

A moiety M² can function as a "spacer" for adjusting the positioning of the heteroaromatic moieties M¹ or M⁴ relative to the dsDNA base pairs at the binding site. As a compound (I) binds in the minor groove, the alignment of heteroaromatic moieties M¹ and M⁴ with the DNA base pairs with which they to interact of optimal binding or sequence recognition may drift as the number of heteroaromatic moieties $M^1$ and $M^4$ increases. Alternatively, incorporation of a moiety $M^2$ adds flexibility to compound (I), allowing its curvature to more accurately match that of the minor groove. The incorporation of one or more flexible moieties $M^2$ relaxes the curvature of the compound backbone, permitting larger compounds (I) to bind to longer sequences of DNA. In some preferred embodiments a moiety $M^2$ is present for every 4 to 5 heteroaromatic moieties $M^1$ or $M^4$, more preferably interrupting long sequences of $M^1$ and/or $M^4$ groups.

Preferred moieties $M^2$ are those corresponding to glycine ($x=0$ in formula III, depicted as IIIa below) and β-alanine ($n=1$ and $R^{15}=H$ in formula III; depicted as IIIb below, hereinafter "β"), with the latter being especially preferred.

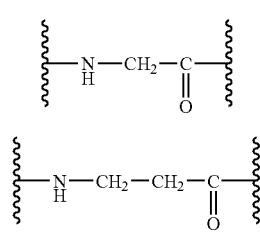

Moieties $M^2$ in which $x=1$ and $R^{15}=OH$, $NH_2$, or F can be used to alter the binding affinity and specificity (relative to β-alanine), as disclosed in Floreancig et al., *J. Am. Chem. Soc.*, 2000, 122, 6342; the disclosure of which is incorporated herein by reference.

When present in compound (I), optional moieties $M^3$ (formula IV)

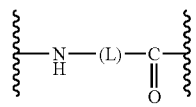

have a group L providing a spacer of 3 to 4 atoms between —NH— and —C(=O)— and can be used to introduce a hairpin turn into compound (I). See Mrksich et al., *J. Am. Chem. Soc.* 1994, 116, 7983. Exemplary moieties $M^3$ include:

(IVa)

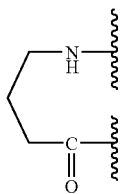

(IVb)

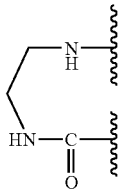

(IVc)

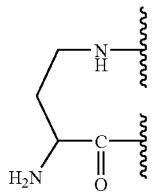

(IVd)

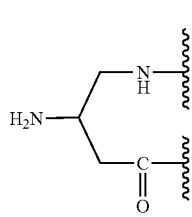

(IVe)

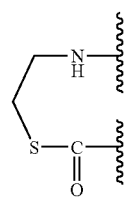

(IVf)

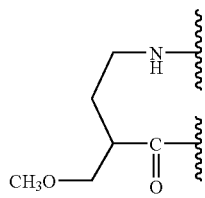

(IVg)

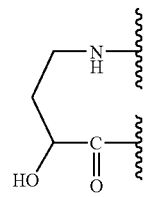

(IVh)

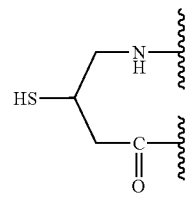

(IVi)

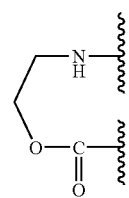

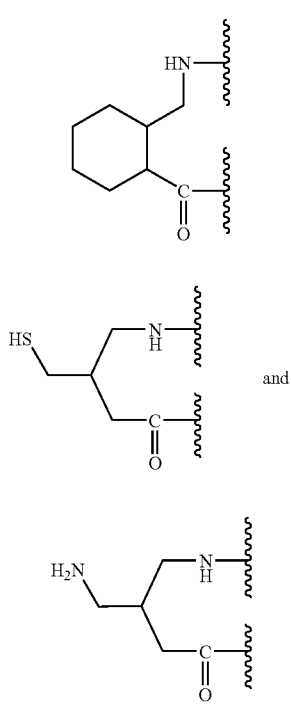

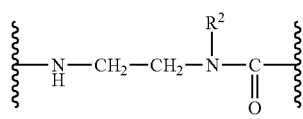

where $R^2$ is as previously defined.

While the group L preferably provides a 3-atom separation between the —NH— and the —(C=O)—, a 4-atom separation is also permissible, as illustrated by a 5-aminovaleric acid residue (i.e., L equals —(CH$_2$)$_4$—):

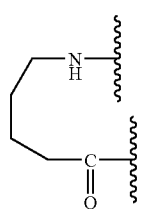

L can have pendant groups, which serve to enhance solubility or function as attachment points for other groups (e.g., IVc, IVd, IVg, IVh, IVk, IVl). The 3 to 4 atoms can be part of a larger group, which provides conformational rigidity (e.g., IVj). The 3 to 4 atoms can comprise carbon atoms only or it can include heteroatoms (e.g., IVb, IVe, IVi).

Moieties $M^4$ are used to introduce a benzamide unit into compound (I). Preferably, the benzamide unit is para-oriented, as in

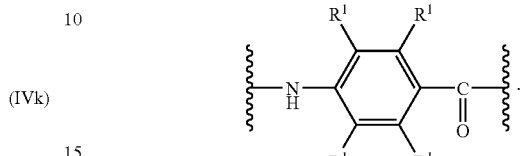

The group $Z(R^2)_n$ can be viewed as a terminal group, located at the C-terminus of compound (I), forming an amide or ester cap there. In the case of Z is N, the two groups $R^2$ can be linked to each other to form a cyclic structure. A group $Z(R^2)_n$ can contain a basic group (as defined hereinbelow). Examples of suitable groups containing a basic group include:

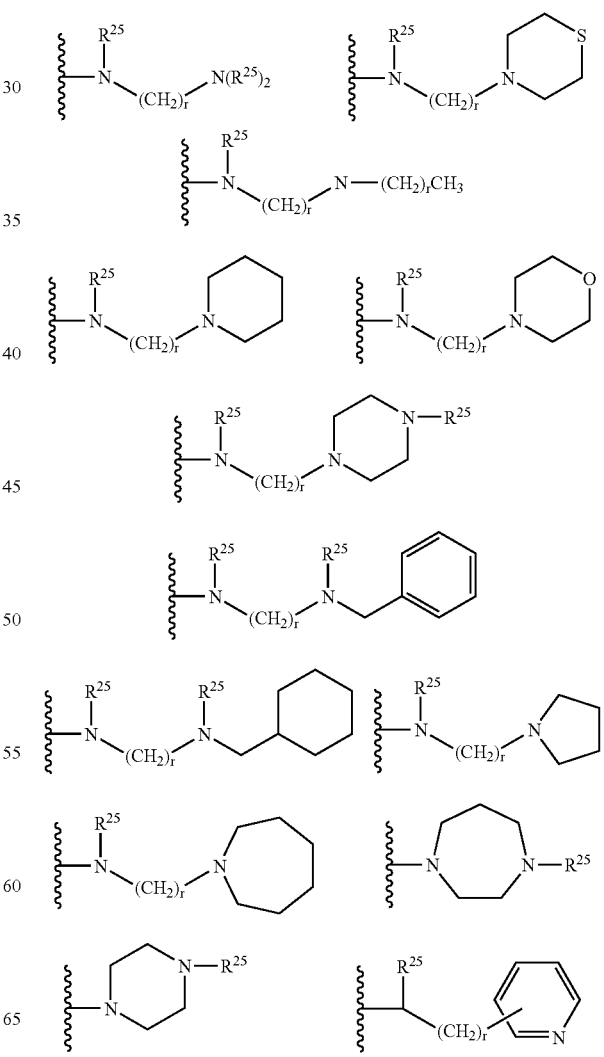

Moieties IVa (hereinafter "γ"), corresponding to γ-aminobutyric acid, and IVc, corresponding to 2,4-diaminobutyric acid, are preferred. Selecting one enantiomer or the other of moieties $M^3$ that are chiral allows stereochemical control of the binding of polyamides to the minor groove, for example as disclosed in Baird et al., WO 98/45284 (1998) in respect of R-2,4-diaminobutyric acid and S-2,4-diaminobutyric acid (corresponding to R-IVc and S-IVc, respectively).

Yet another class of moieties $M^3$ is represented by the formula

-continued

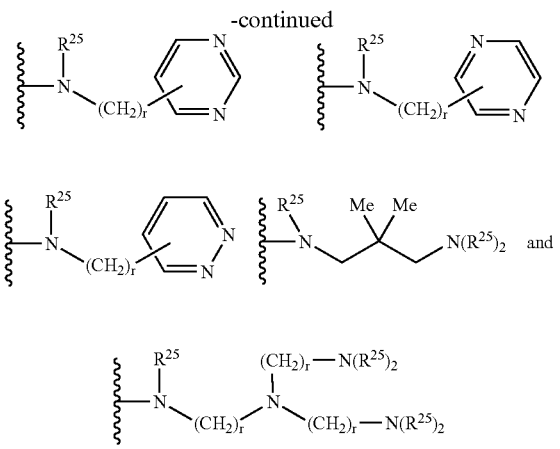

Examples of suitable groups $Z(R^2)_n$ not containing a basic group include:

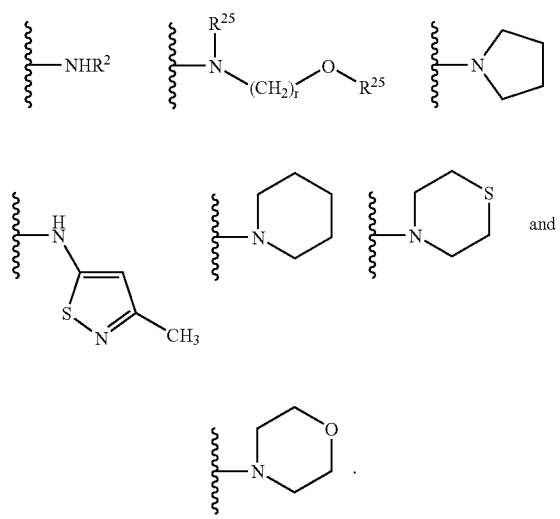

Figure 5:
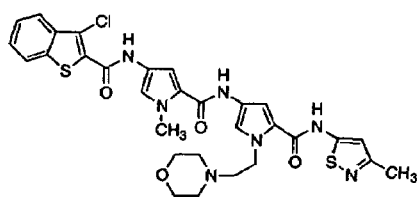
Figure 5:
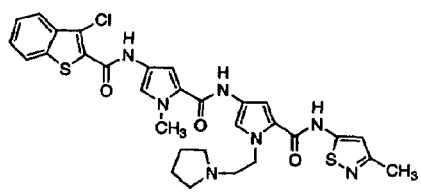
Figure 5:
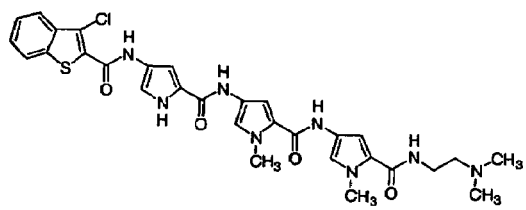
Figure 5:
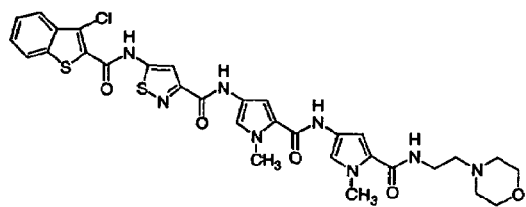
Figure 5:
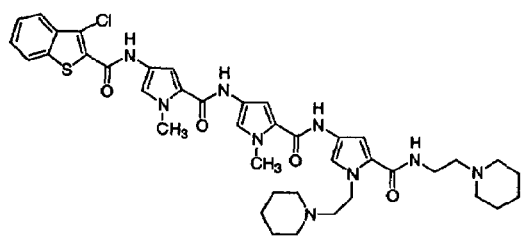
Figure 5:
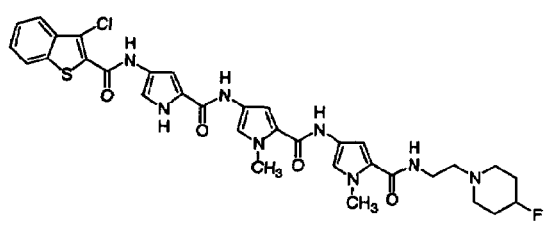
Figure 5:
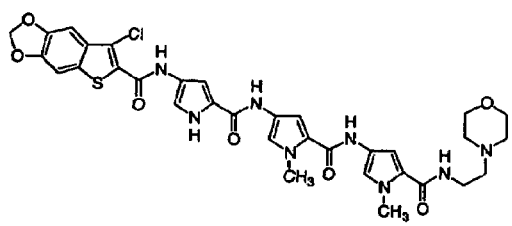
Figure 5:
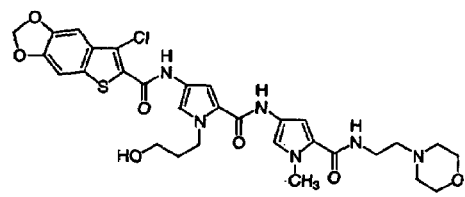
Figure 5:
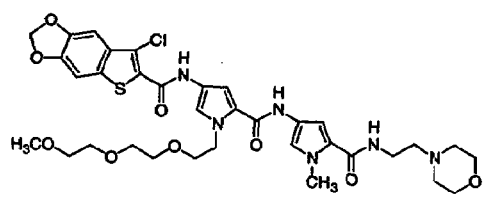
Figure 5:
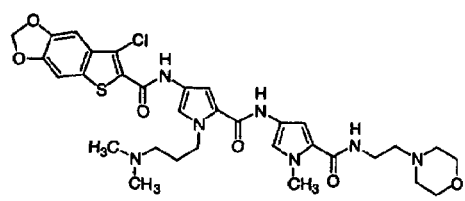
Figure 6:
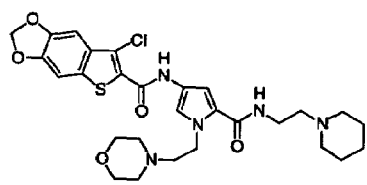
Figure 6:
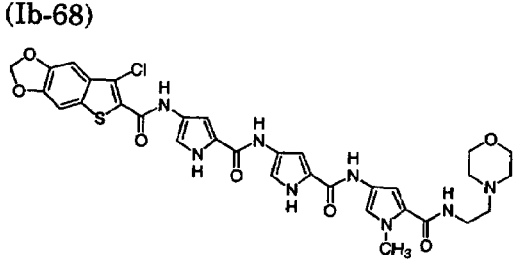
Figure 6:
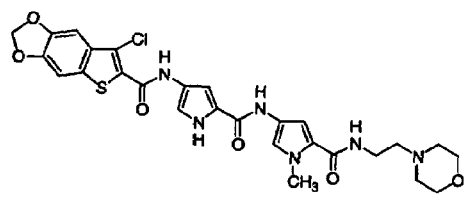
Figure 6:
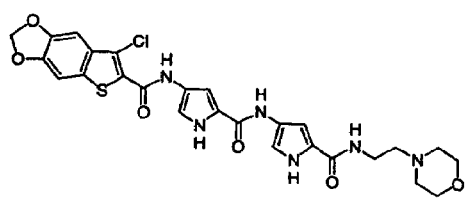
Figure 6:
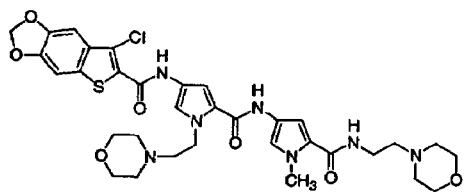
Figure 6:
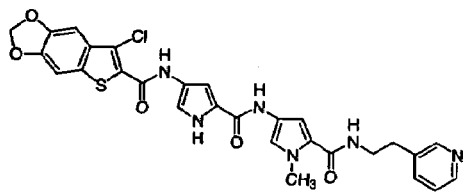
Figure 6:
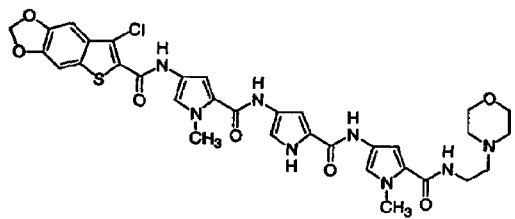
Figure 6:
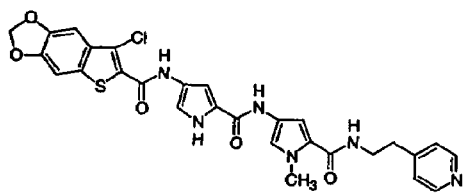
Figure 6:
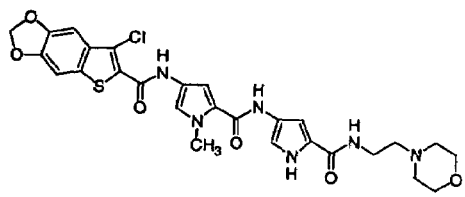
Figure 6:
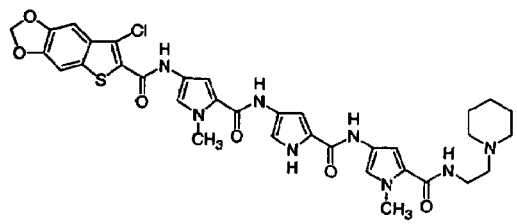
Figure 7:
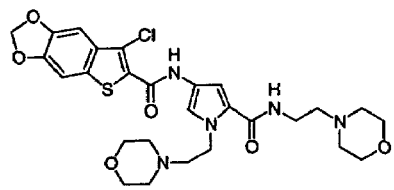
Figure 7:
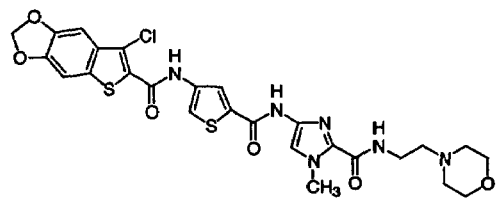
Figure 7:
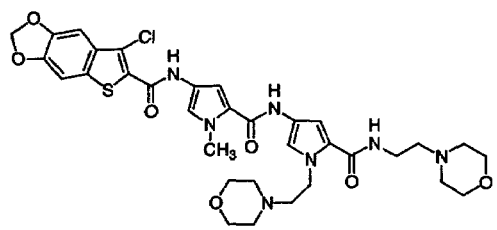
Figure 7:
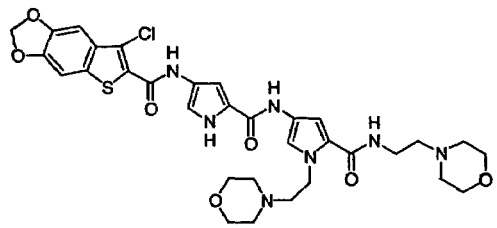
Figure 7:
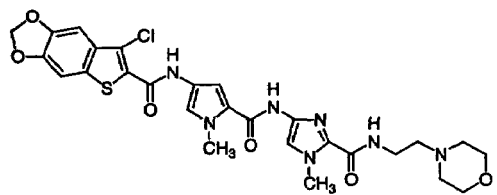
Figure 7:
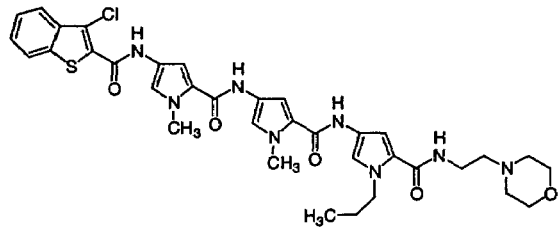

The classification of the 5-amino-2-methylisothiazole group as a "nonbasic" $Z(R^2)_n$ group is somewhat arbitrary, as its $pK_b$ is marginal, normally around 12–13 (i.e., $pK_a$ 1–2) and depending on the molecular structure of the entire compound, it may qualify or not as a basic group as such is defined herein. Preferably, where a 5-amino-2-methyl-isothiazole is present, the compound has a basic group elsewhere in the molecule, for example pendant from a moiety $M^1$ or $M^4$, as exemplified by compounds Ib-53 and Ib-54 in FIG. 5.

In the foregoing formulae, r is an integer ranging from 2 to 8, inclusive (preferably 2 to 6), and each $R^{25}$ is independently H, $CH_3$, $CH_2CH_3$, $CH_2CH_2CH_3$, or $CH(CH_3)_2$.

The preceding illustrative formulae of basic and nonbasic groups $Z(R^2)_n$ have been drawn with Z being N and n being 2 for convenience. Those skilled in the art will appreciate that these illustrations can be replaced with the alternative embodiment in which Z is O and n is 1. Where Z is O, preferably the adjacent moiety Y is Py.

As used herein with reference to groups $R^1$ and $R^2$, "substituted or unsubstituted ($C_1$–$C_{12}$)alkyl group, or a substituted or unsubstituted ($C_1$–$C_{12}$)heteroalkyl group" includes not only conventional alkyl or cycloalkyl groups such as methyl, ethyl, propyl, isopropyl, butyl, s-butyl, isobutyl, t-butyl, cyclopentyl, cyclohexyl, and pentyl, but also unsaturated $C_1$ to $C_{12}$ groups, having for example aromatic, alkenyl, or alkynyl groups (e.g., phenyl, benzyl, vinyl, cyclohexenyl, etc.). One or more backbone carbons can be replaced by heteroatoms. There may be present functionalities such as hydroxy; oxo (=O); primary, secondary, or tertiary amine (e.g., —$NH_2$, —$NH(CH_3)$, —$N(CH_3)_2$); quaternary ammonium (e.g., —$N(CH_3)_3^+$); alkoxy (e.g., methoxy, ethoxy); acyl (e.g., —C(=O)$CH_3$); amide (e.g., —NHC(=O)$CH_3$); thiol; thioether (e.g., —$SCH_3$); sulfoxide; sulfonamide (e.g., —$SO_2NHCH_3$); halogen (e.g., F, Cl); nitro; and the like. Exemplary specific $R^1$, $R^2$, and $R^5$ groups include methyl, trifluoromethyl, ethyl, acetyl, methoxy, methoxyethyl, ethoxyethyl, aminoethyl, hydroxyethyl, propyl, hydroxypropyl, cyclopropyl, isopropyl, 3-(dimethylamino)propyl, butyl, s-butyl, isobutyl, t-butyl, pentyl, cyclopentyl, vinyl, allyl, ethynyl, propynyl, and the like.

Compound (I) preferably has a basic group having a $pK_b$ of 12 or less or a quaternized nitrogen group. (Or, stated conversely, the conjugate acid of the basic group has a $pK_a$ greater than 2 ($pK_a$=14–$pK_b$).) Preferably, the $pK_b$ is less than 10, more preferably less than 5. A $pK_b$ of less than 12 ensures that compound (I) is protonated under the conditions in which it interacts with a nucleic acid. Preferably the basic group is a nitrogenous group, for example an amine, an amidine, a guanidine, a pyridine, a pyridazine, a pyrazine, a pyrimidine, an imidazole, or an aniline. Primary, secondary, or tertiary aliphatic amines, are preferred. Exemplary quaternized nitrogen groups include alkyl pyridinium and tetraalkyl ammonium groups such as:

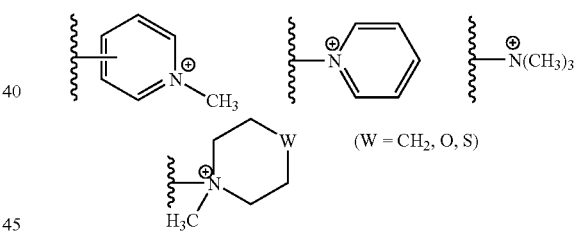

(W = $CH_2$, O, S)

Without being bound by theory, it is believed that the basic group enhances cell transport properties, enabling the compounds of this invention to be transported across cellular and nuclear membranes and to reach dsDNA in the nucleus. See Rothbard et al., WO 98/52614 (1998), which discloses that guanidine or amidino side chain moieties enhance transport across biological membranes. Another possible benefit is enhancement of the binding affinity to the nucleic acid, perhaps via ionic interactions with backbone phosphate groups. See Baird and Dervan, WO 98/37087 (1998) and Bruice et al., U.S. Pat. No. 5,698,674 (1997). Lastly, the protonated basic group enhances the solubility of compounds (I).

Preferably, the basic group is present within the C-terminal group $Z(R^2)_n$, but it may be present elsewhere in the molecule, for example as part of a group $R^1$ or $R^2$ in $M^1$ or $M^4$. Or, multiple basic groups may be present, at different parts of compound (I).

In a preferred embodiment, compound (I) is according to formula (Ia):

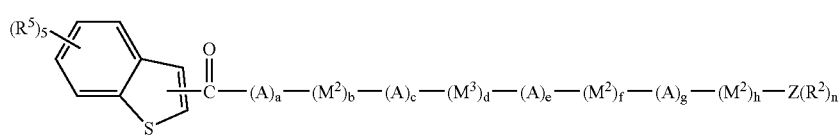

(Ia)

wherein $M^2$, $M^3$, $R^2$, $R^5$, Z and n have the same meanings as previously assigned; each A is independently $M^1$ or $M^4$; each of a, c, e, g and h is an integer independently from 0 to 5, inclusive; and each of b, d, and f is independently 0 or 1. The sum of a, c, e, and g is at least 2, preferably at least 3. In one preferred embodiment, each A is $M^1$. Also preferably, the moiety A associated with the subscript a is a moiety $M^1$.

In another preferred embodiment, compound (I) is according to formula (Ib):

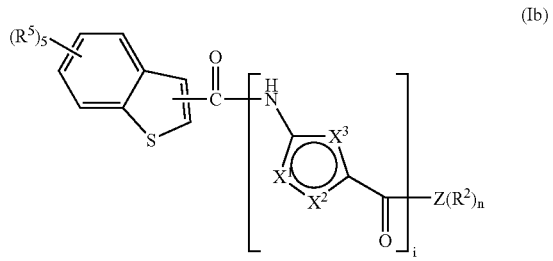

(Ib)

wherein $X^1$, $X^2$, $X^3$, $R^2$, $R^5$, Z, and n have the meanings previously assigned and i is an integer from 1 to 4, inclusive. In one subset of compounds according to formula (Ib), each of the moieties

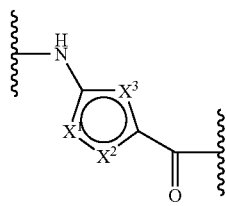

is Py, with Table 1 listing exemplary such compounds (Ib):

TABLE 1

Illustrative Compounds (Ib)

| Compound Ref. | ![benzothiophene-C(O)] | i | Z(R²)ₙ |
|---|---|---|---|
| Ib-1 | 3-Cl-benzothiophene-2-C(O)– | 3 | –NH–CH₂CH₂–morpholine |
| Ib-2 | Same | 3 | –NH–CH₂CH₂–C(=NH)NH₂ |
| Ib-3 | benzothiophene-2-C(O)– | 2 | –NH–CH₂CH₂–morpholine |

TABLE 1-continued

Illustrative Compounds (Ib)

| Compound Ref. | (R⁵)₅—[benzothiophene]—C(=O)— | i | —Z(R²)ₙ |
|---|---|---|---|
| Ib-4 | 3-chloro-benzothiophen-2-yl-C(=O)— | 2 | Same |
| Ib-5 | Same | 3 | —NH—CH₂CH₂CH₂—morpholinyl |
| Ib-6 | Same | 3 | —NH—CH₂CH₂—thiomorpholinyl |
| Ib-7 | Same | 3 | —NH—CH₂CH₂—piperidinyl |
| Ib-8 | Same | 2 | Same |
| Ib-9 | Same | 2 | —NH—CH₂CH₂—thiomorpholinyl |
| Ib-10 | 6-fluoro-3-chloro-benzothiophen-2-yl-C(=O)— | 3 | —NH—CH₂CH₂—morpholinyl |
| Ib-11 | 5-fluoro-3-chloro-benzothiophen-2-yl-C(=O)— | 2 | Same |
| Ib-12 | Same | 3 | —NH—CH₂CH₂—thiomorpholinyl |
| Ib-13 | 3-chloro-benzothiophen-2-yl-C(=O)— | 3 | —NH—CH₂CH₂—N(CH₂CH₃)₂ |

TABLE 1-continued

Illustrative Compounds (Ib)

| Compound Ref. | (R⁵)₅-benzothiophene-C(=O)- structure | i | -Z(R²)ₙ |
|---|---|---|---|
| Ib-14 | Same | 3 | -NH-CH₂CH₂-pyrrolidin-1-yl |
| Ib-15 | Same | 3 | -NH-CH₂CH₂-N(2,6-dimethylmorpholin-4-yl) |
| Ib-16 | Same | 3 | -NH-CH₂CH₂-(pyridin-2-yl) |
| Ib-17 | Same | 3 | -NH-CH₂CH₂-(pyridin-3-yl) |
| Ib-18 | Same | 3 | -NH-CH₂CH₂-(pyridin-4-yl) |
| Ib-19 | Same | 2 | -NH-CH₂CH₂-NH-C(=NH)NH₂ |
| Ib-20 | benzo[b]thiophen-3-yl-C(=O)- | 3 | -NH-CH₂CH₂-morpholin-4-yl |
| Ib-20a | 3-chlorobenzo[b]thiophen-2-yl-C(=O)- | 2 | -NH-CH₂CH₂-(4-hydroxypiperidin-1-yl) |
| Ib-20b | Same | 3 | -NH-CH₂CH₂-(4-methyl-4-morpholinium) |

TABLE 1-continued
Illustrative Compounds (Ib)
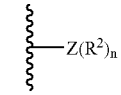
| Compound Ref. | | i | |
|---|---|---|---|
| Ib-20c | 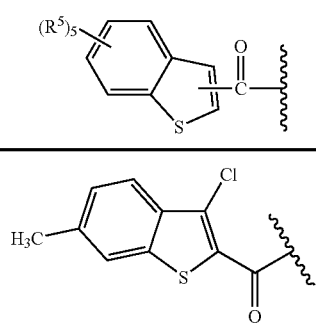 | 3 | 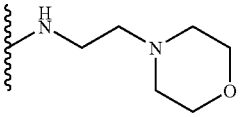 |
| Ib-20d | 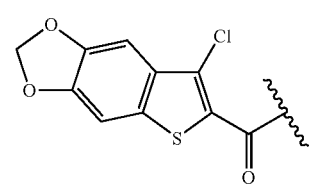 | 3 | 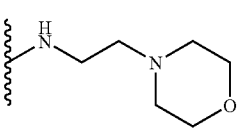 |
| Ib-20e | Same | 2 | Same |
| Ib-20f | Same | 1 | Same |
| Ib-20g | Same | 3 | 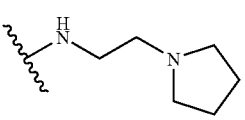 |
| Ib-20h | Same | 3 | 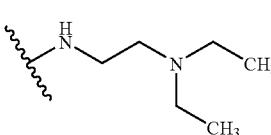 |
| Ib-20i | Same | 3 | 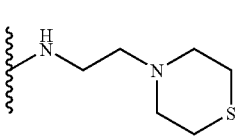 |
| Ib-20j | 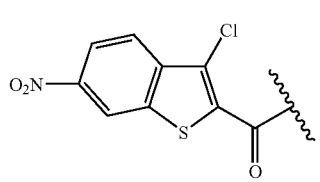 | 3 | 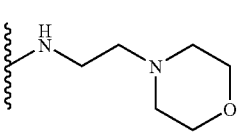 |
| Ib-20k | 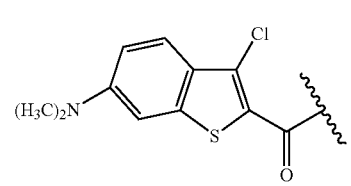 | 3 | Same |
| Ib-20l | 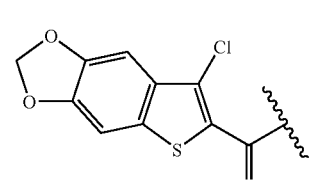 | 3 | 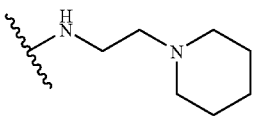 |

TABLE 1-continued

Illustrative Compounds (Ib)

| Compound Ref. | (R⁵)₅–[benzothiophene]–C(=O)– structure | i | –Z(R²)ₙ structure |
|---|---|---|---|
| Ib-20m | Same | 3 | –NH–CH₂CH₂–(1-methylpyrrolidin-2-yl) |
| Ib-20n | Same | 1 | –NH–CH₂CH₂–piperidin-1-yl |
| Ib-20o | Same | 1 | –NH–CH₂CH₂–pyrrolidin-1-yl |
| Ib-20p | methylenedioxy-, Cl-substituted benzothiophene-C(=O)– | 1 | –NH–CH₂CH₂–thiomorpholin-4-yl |
| Ib-20q | Same | 1 | –NH–CH₂CH₂–(4,4-difluoropiperidin-1-yl) |
| Ib-20r | Same | 1 | –NH–CH₂CH₂CH₂–(4-methylpiperazin-1-yl) |
| Ib-20s | F-, Cl-substituted benzothiophene-C(=O)– | 2 | CH₃–NH–CH₂CH₂CH₂–N(CH₃)₂ |
| Ib-20t | methylenedioxy benzothiophene-C(=O)– | 1 | –NH–CH₂CH₂–morpholin-4-yl |
| Ib-20u | Same | 2 | Same |
| Ih-20v | Same | 3 | Same |
| Ib-20w | Same | 1 | –NH–CH₂CH₂–thiomorpholin-4-yl |

TABLE 1-continued

Illustrative Compounds (Ib)

| Compound Ref. | (R⁵)₅—[benzothiophene]—C(=O)—⁂ | i | ⁂—Z(R²)ₙ |
|---|---|---|---|
| Ib-20x | Same | 1 | ⁂—NH—CH₂CH₂—N(pyrrolidine) |
| Ib-20y | HO, HO, Cl substituted benzothiophene-2-C(=O)— | 1 | ⁂—NH—CH₂CH₂—N(morpholine) |

However, in formula Ib the moieties

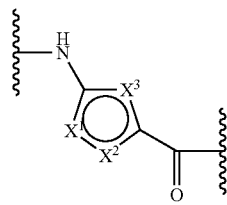

need not all be Py. They can include other 5-member ring heterocycles, as illustrated by the compounds shown in FIGS. 1 through 7.

A preferred sub-embodiment according to formula (Ib) is

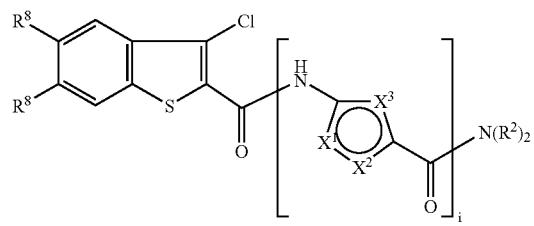

where one $R^8$ is H and the other $R^8$ is H, F, $CH_3$, $NO_2$, or $N(CH_3)_2$ and $X^1$, $X^2$, $X^3$, i, and $R^2$ are as previously defined.

A second preferred sub-embodiment is

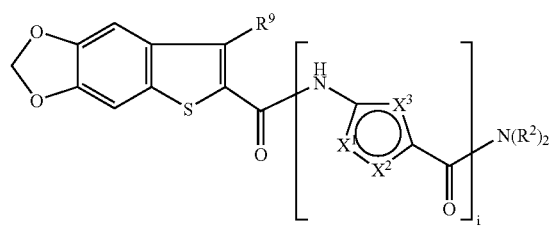

where $R^9$ is Cl or H and $X^1$, $X^2$, $X^3$, i, and $R^2$ are as previously defined.

A third preferred sub-embodiment is

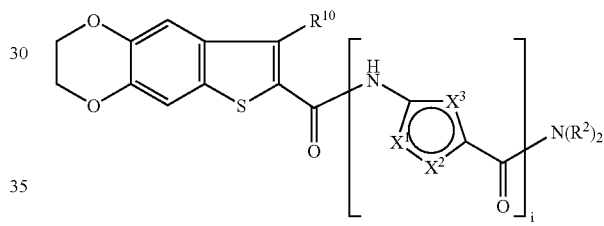

where $R^{10}$ is Cl or H and $X^1$, $X^2$, $X^3$, i, and $R^2$ are as previously defined.

Examples of the foregoing sub-embodiments according to formula (Ib) are found in Table 1 and FIGS. 1 through 7.

In another preferred embodiment, compound (I) is according to formula (Ic):

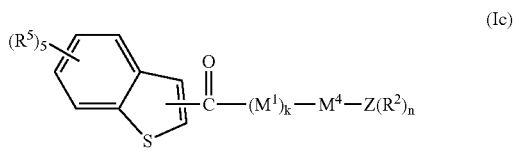

(Ic)

wherein $M^1$, $M^4$, $R^2$, $R^5$, Z and n are as previously defined and k is an integer from 0 to 2 (preferably 0 or 1, more preferably 1), inclusive.

In another preferred embodiment, compound (I) is according to formula (Id):

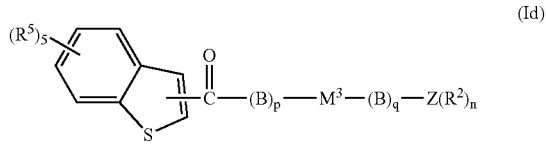

Figure 8:
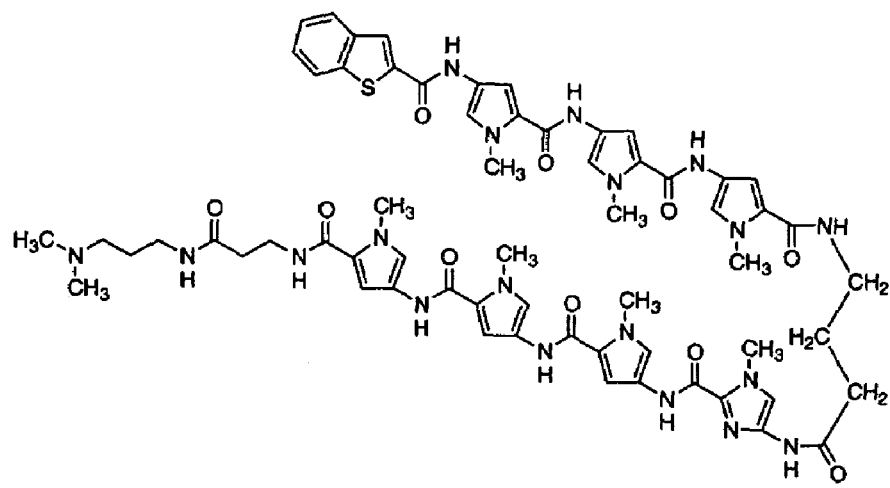
Figure 8:
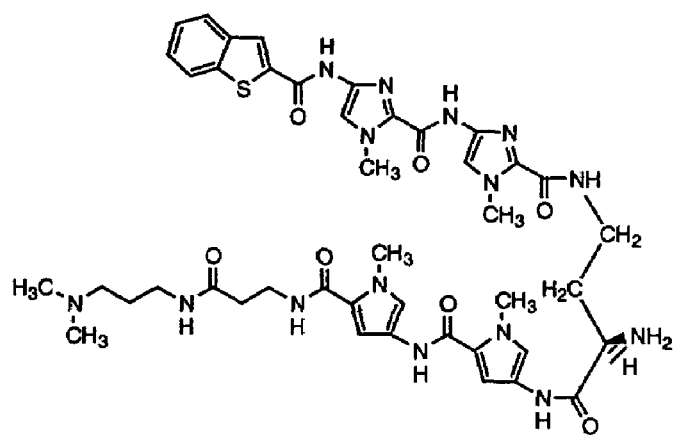
Figure 8:
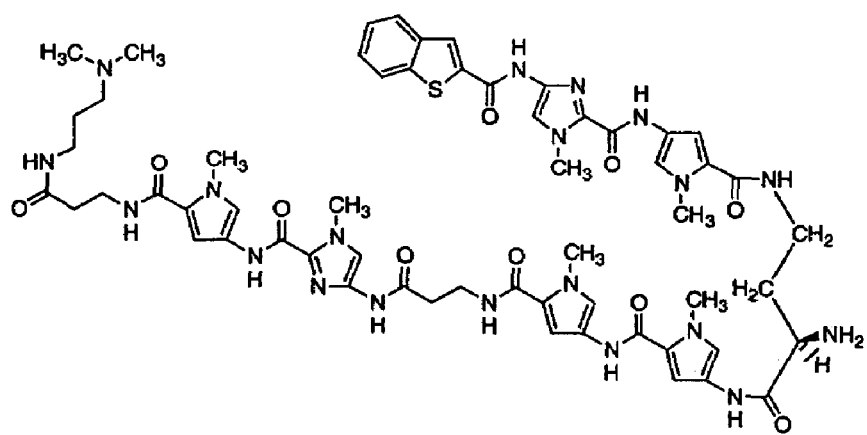
Figure 9:
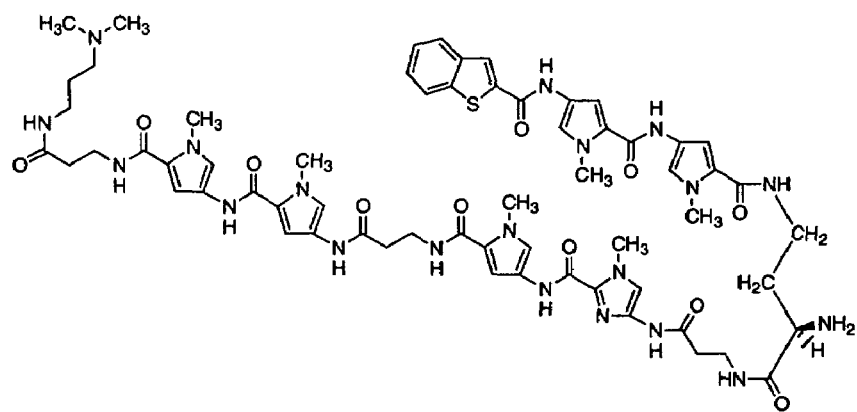
Figure 9:
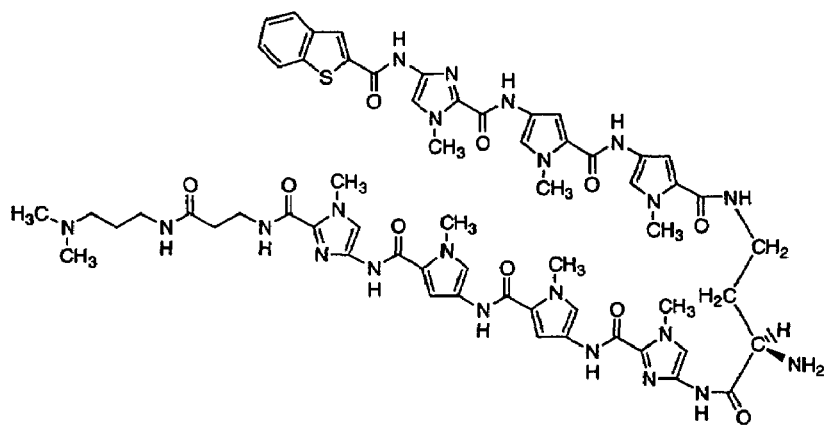

(Id)

wherein $M^3$, $R^2$, $R^5$, Z and n are as previously defined; each B is independently $M^1$ or $M^2$; and p and q are independently integers from 1 to 7, inclusive (more preferably 2 to 4, inclusive). Exemplary compounds (Id) include compounds Id-1 through Id-5, whose structures are depicted in FIGS. 8 and 9.

In another preferred embodiment, compound (I) is according to formula (Ie):

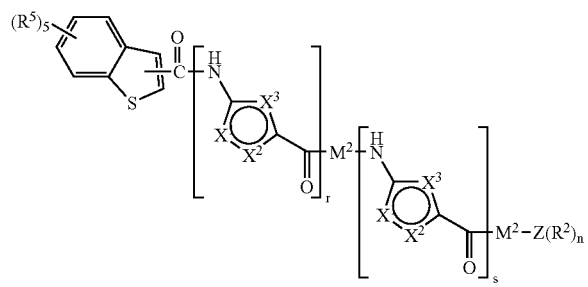

Figure 10:
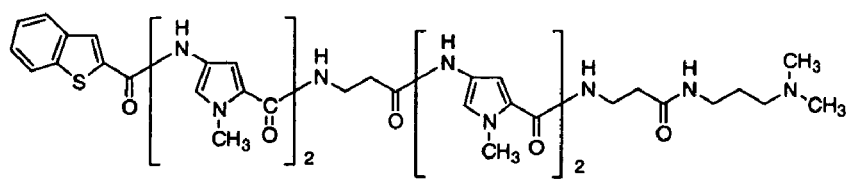
Figure 10:
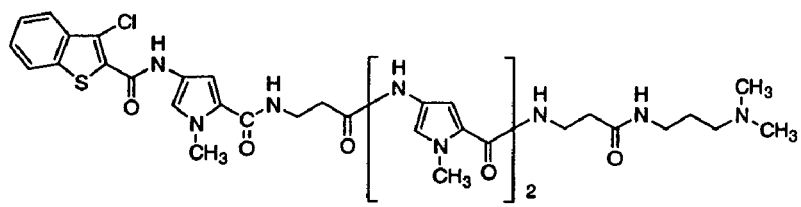
Figure 10:
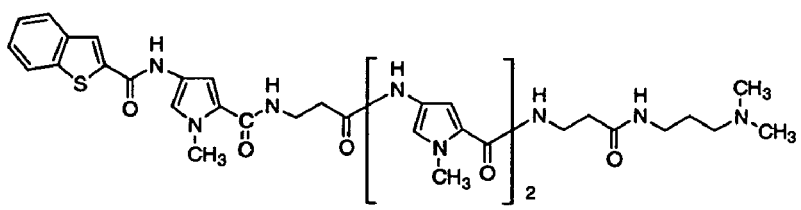
Figure 10:
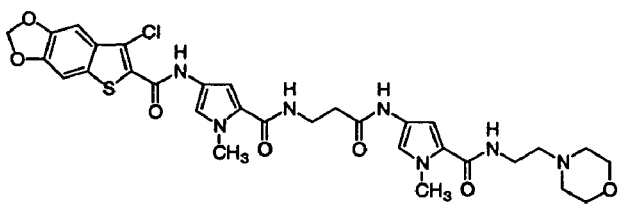

(Ie)

wherein $X^1$, $X^2$, $X^3$, $M^2$, $R^2$, $R^5$, Z, and n are as previously defined and each of r and s is independently 1 or 2. Exemplary compounds (Ie) include compounds Ie-1 through Ie-4, whose structures are depicted in FIG. 10.

Compounds (I) can be conjugated or linked to another nucleic acid binding compound. The conjugated nucleic acid binding compounds can be two identical or different compounds (I), or one compound (I) and a different class of nucleic acid binder, for example an intercalator, a triple helix former, a binder to the phosphate backbone, a major groove binder, another type of minor groove binder, and the like. A preferred site for forming the conjugating link is an amino, hydroxy, or thiol functionality in a group L in moiety $M^2$, which can be acylated or alkylated. The preparation of tandem linked nucleic acid binding polyamides in this manner is disclosed in Baird et al., WO 98/45284 (1998), the disclosure of which is incorporated herein by reference.

Compounds (I) also can be conjugated to other moieties, such as, peptides, proteins, transport agents, fluorophores or other reporter groups, and the like.

Compounds (I) preferably bind to dsDNA with high affinity, meaning an equilibrium dissociation constant of $10^{-3}$ M or less, more preferably $10^{-6}$ M or less, and most preferably $10^{-9}$ M or less. The measurement of binding affinities by quantitative DNase I footprinting is disclosed in Dervan, WO 98/50582 (1998), and Trauger et al., Nature 382, 559 (8 Aug. 1996); the disclosures of which are incorporated herein by reference, and is also described in the examples hereinbelow.

Compounds of this invention can be used to form complexes with dsDNA, for the purpose of recognizing and/or isolating dsDNA strands containing particular base-pair sequences, for example for analytical or diagnostic purposes. Thus, in another aspect of this invention there is provided a complex between dsDNA and compound of this invention. In cellular systems or in living organisms, they can modulate the expression of a gene by binding to the gene or a promoter or repressor region thereof. Such modulation may be useful for therapeutic or research purposes.

Additionally, compounds of this invention have been found to have anti-bacterial and/or properties and therefore may be used for combating (i.e., preventing and/or treating) infections in eukaryotic organisms, especially mammals.

Other pathogens against which compounds of this invention can be useful include fungi, protozoa and viruses. For human anti-infective applications, an effective amount of a compound of this invention is used, optionally in combination with a pharmaceutically acceptable carrier. The composition may be dry, or it may be a solution. Treatment may be reactive, for combating an existing infection, or prophylactic, for preventing infection in an organism susceptible to infection. Preferably, compounds of this invention are used to treat infections by Gram-positive bacteria, in particular drug-resistant strains thereof, for example MRSA (methicillin resistant *S. aureus*), MRSE (methicillin resistant *S. epidermidis*), PRSP (penicillin resistant *S. pneumoniae*) or VRE (vancomycin resistant *Enterococci*). By "drug-resistant" it is meant that the bacteria are resistant to treatment with conventional antibiotics.

Host organisms that can be treated include eukaryotic organisms, in particular plants and animals. The plant may be an agriculturally important crop, such as wheat, rice, corn, soybean, sorghum, and alfalfa. Animals of interest include mammals such as bovines, canines, equines, felines, ovines, porcines, and primates (including humans). Thusly, in another aspect of this invention, there is provided a method for treating a bacterial infection—particularly an infection by Gram-positive bacteria—comprising administering to a patient in need of such treatment an effective amount of compound (I). Compounds of this invention can also be used for the preparation of a medicament for the treatment of a bacterial infection in mammals. The compounds may be administered orally, topically, or parenterally (e.g., intravenously, subcutaneously, intraperitoneally, transdermally).

While not wishing to be bound by any particular theory, it is believed that the compounds of this invention derive their biological activity from their ability to bind to dsDNA, in particular promoter regions of genes essential for pathogen survival and interfering with the expression of such essential genes.

Compounds I can be synthesized by solid phase techniques from the corresponding amino acids or their derivatives, for instance IIc', IId', and IIe' for the synthesis of the Py, Hp, and Im building blocks, respectively.

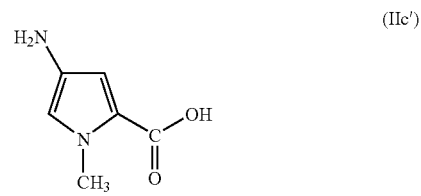

(IIc')

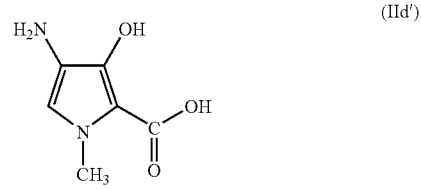

(IId')

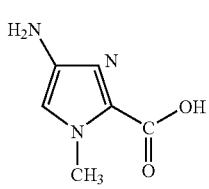

In solid phase synthesis, a polyamide is synthesized on a resin such as Boc-glycine-PAM-resin or Boc-β-alanine-PAM-resin, with moieties Y being added in series of steps involving amino-protected and carboxy-activated monomers, as taught in Dervan et al., U.S. Pat. No. 6,090,947 (2000); Baird et al., WO 98/37066 (1998); Baird et al., WO 98/37067 (1998); and Dervan et al., WO 98/49142 (1998); the disclosures of which are incorporated herein by reference. Alternatively, combinatorial synthetic techniques can be employed. See, for example, Boger et al., *J. Am. Chem. Soc.* 2000, 122, 6382–6394, also incorporated herein by reference.

The practice of this invention may be further understood by reference to the following examples, which are provided by way of illustration and not of limitation.

EXAMPLE A

This example describes the synthesis of intermediates for the preparation of compounds of this invention having pyrrole carboxamide units in which the pyrrole nitrogen is substituted with a substituent other than methyl, as in the instance of compounds Ib-29, Ib-31 to Ib-34, Ib-36 to Ib-46, Ib-50 to Ib-51. A general method for the preparation of the above-mentioned intermediates is given in the Scheme 1.

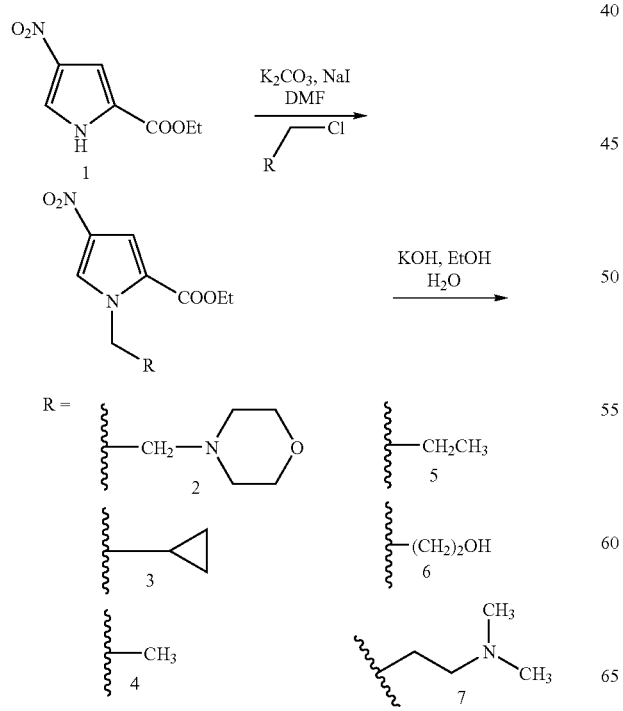

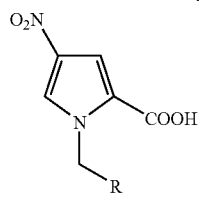
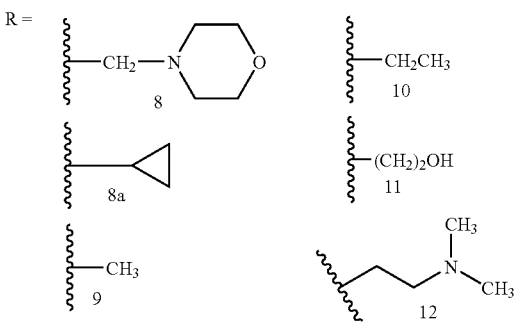
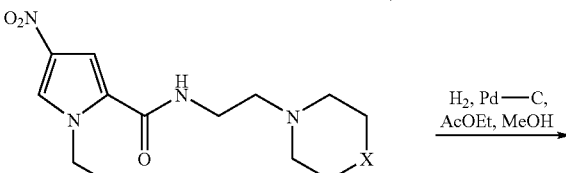
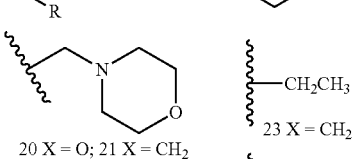
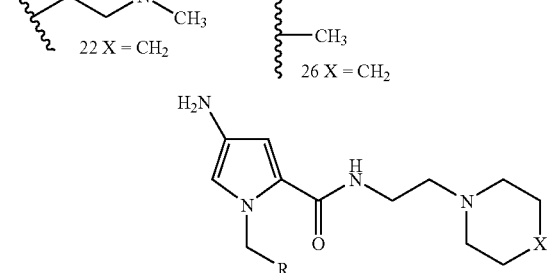
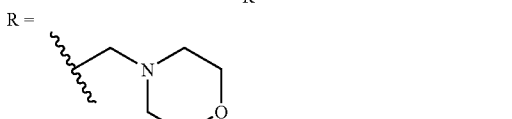
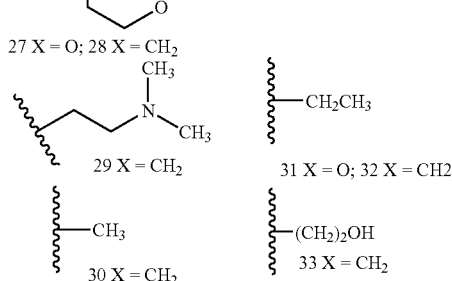
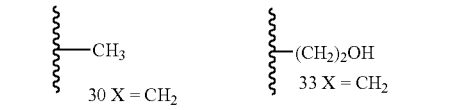

Synthesis of Compounds 2–7. The synthesis of compounds 2–7 is illustrated with specific reference to compound 2, the other compounds being analogously synthesizable. A mixture of ethyl 4-nitropyrrole-2-carboxylate 1 (20.00 g, 1.0 equiv.), 4-(2-chloroethyl)-morpholine hydrochloride (28.28 g, 1.4 equiv.), NaI (16.28 g, 1.0 equiv.) and $K_2CO_3$ (28.78 g, 1.92 equiv.) in DMF (200 mL) was stirred at 60° C. for 10.5 h and poured into a mixture of $H_2O$ and saturated aq. $K_2CO_3$ (550/50 mL). The resulting solution was extracted with AcOEt (4×, each 200 mL). The combined organic layers were dried ($MgSO_4$) and evaporated to give compound 2 as pale yellow crystals (31.4 g, 97%). The $^1$H-NMR spectrum was consistent with the structure of compound 2.

Synthesis of Compounds 8–12. The synthesis of compounds 8–12 is illustrated with specific reference to compound 8, the other compounds being analogously synthesizable. A suspension of the ester 2 (31.4 g, 1.0 equiv.) and KOH (8.13 g, 2 equiv.) in EtOH (100 mL) and $H_2O$ (100 mL) was stirred at RT for 16 h (complete dissolution occurred after 1 h). The mixture was acidified with 1M aq. HCl to pH=3.0 and the resulting precipitate was collected by filtration and dried in vacuo to give compound 8 as white solids (23.0 g, 81%). The $^1$H-NMR spectrum was consistent with the structure of compound 8.

Synthesis of Compounds 20–26 and 27–33. The synthesis of compounds 20–26 and 27–33 is illustrated with specific reference to compounds 20 and 27, the other compounds being analogously synthesizable. A mixture of the acid 8 (1.5 g, 1.0 equiv.) and HBTU (2-(1H-benzotriazole-1-yl)-1,1,3,3-tetramethyluronium hexafluorophosphate) (1.8 g, 1 equiv.) in DMF (8 mL) and DEA (diisopropyl-ethylamine) (2 mL) was stirred at RT for 1 h, treated with the 4-(2-aminoethyl)morpholine (0.70 mL, 1.1 equiv.) and stirred for 15 h at RT. The solution was added dropwise to ice water (150 mL) and extracted with AcOEt (5×). The combined organic layers were dried ($MgSO_4$) and evaporated to give compound 20 as brown solids (1.6 g, $^1$H-NMR spectrum was consistent with the structure of 20). The crude product was dissolved in AcOEt (50 mL) and MeOH (5 mL), treated with 10% Pd—C (ca. 100 mg), and stirred at RT under $H_2$ (1 atm) for 48 h. The mixture was filtered through Celite and the solids washed with MeOH. The filtrate was concentrated in vacuo, diluted with $Et_2O$ (250 mL) and AcOEt (50 mL), and treated with HCl (g) for 1 min. Evaporation of the solvents gave compound 27 as orange solids (1.7 g), which was subsequently used without further purification for the preparation of final compounds such as Ib-33 or Ib-34.

EXAMPLE B

This example describes the synthesis of intermediates containing benzothiophene moieties, for coupling with the intermediates prepared in Example A, as illustrated in Scheme 2 with particular reference to 3-chlorobenzothiophene moieties.

Scheme 2

Variation a:

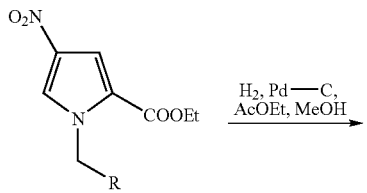

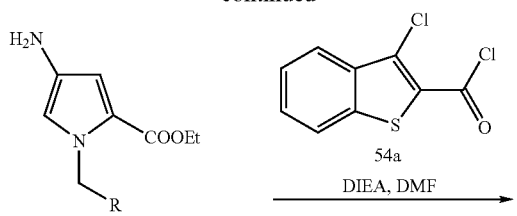

-continued

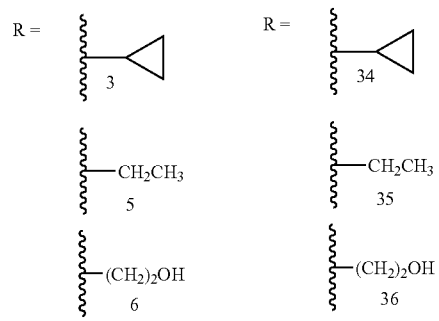

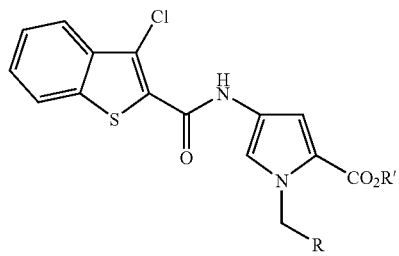

Variation b:

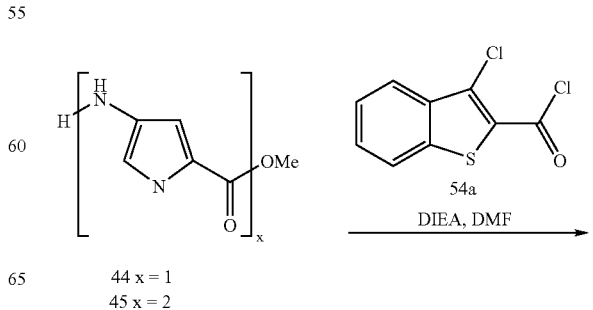

44 x = 1
45 x = 2

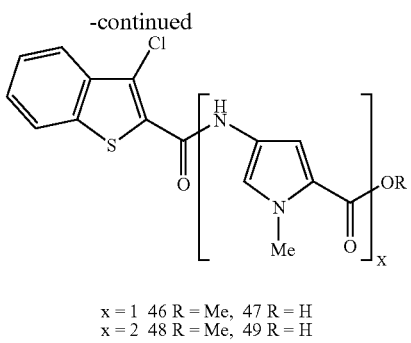

x = 1  46 R = Me, 47 R = H
x = 2  48 R = Me, 49 R = H

Variation a: Synthesis of the Compounds 38 and 43. Variation a pertains to the coupling of a benzothiophene moiety to a pyrrole carboxamide moiety in which the pyrrole nitrogen is substituted with a substituent other than methyl and is illustrated by particular reference to compounds 40 and 41, with compounds 38–39 and 42–43 being analogously synthesizable. A mixture of the amino ester 35 (500 mg, 1.0 equiv.) and the acid chloride 54a (546 mg, 1.1 equiv.) in NMP (4 mL) and DIEA (1 mL) was stirred at 40° C. for 16 h and added to a mixture of ice-water (100 mL) and sat. aqueous $K_2CO_3$ (5 mL). The resulting solids were collected by filtration and dissolved in EtOH (ca. 50 mL), $H_2O$ (40 mL) and 2M aqueous KOH (10 mL). The mixture was stirred at 60° C. for 24 h and washed with $Et_2O$ (1×). The aqueous layer was acidified to pH=1.9 using 1M aqueous HCl and the resulting precipitate collected by filtration and dried in vacuo to give compound 41 as a white solid. The $^1$H-NMR spectrum was in agreement with the structure of 41.

Variation b: Synthesis of Compounds 46 and 49. Variation b pertains to the coupling of a benzothiophene moiety to one or more pyrrole carboxamide moieties in which the pyrrole nitrogens are substituted with methyl groups, using compounds 48 and 49 as examples, with compounds 46 and 47 being analogously synthesizable. A mixture of the acid chloride 54a (8.23 g, 1.1 equiv.) and amine 45 (10.00 g, 1.0 equiv., Bailly et al., J. Pharm. Chem., November 1989, 78 (11), 910–917) in DMF (75 mL) and DIEA (15 mL) was stirred for 23 h at RT (exothermic) and added to a mixture of ice water (1000 mL) and sat. aqueous $K_2CO_3$ (50 mL). The resulting precipitate was collected by filtration and washed ($H_2O$). A small sample was dried in vacuo: the $^1$H-NMR spectrum of this sample was in agreement with the structure of compound 48.

The crude product was suspended in EtOH (150 mL) and $H_2O$ (150 mL), treated with KOH (10 g) and stirred at 60° C. for 7 h. The mixture was diluted with $H_2O$ (to a volume of ca. 700 mL), washed with AcOEt (1×) and acidified to pH=2.4 using 6M aqueous HCl. The solids were collected by filtration and dried in vacuo to give acid 49 (12.4 g, 85%, two steps). The $^1$H-NMR spectrum was in agreement with the structure of compound 49.

EXAMPLE C

In this example, intermediates synthesized per Examples A and B (variation a) are coupled to provide compounds of this invention. The synthetic scheme is summarized in Scheme 3 and a detailed representative procedure is provided with specific reference to compound Ib-39.

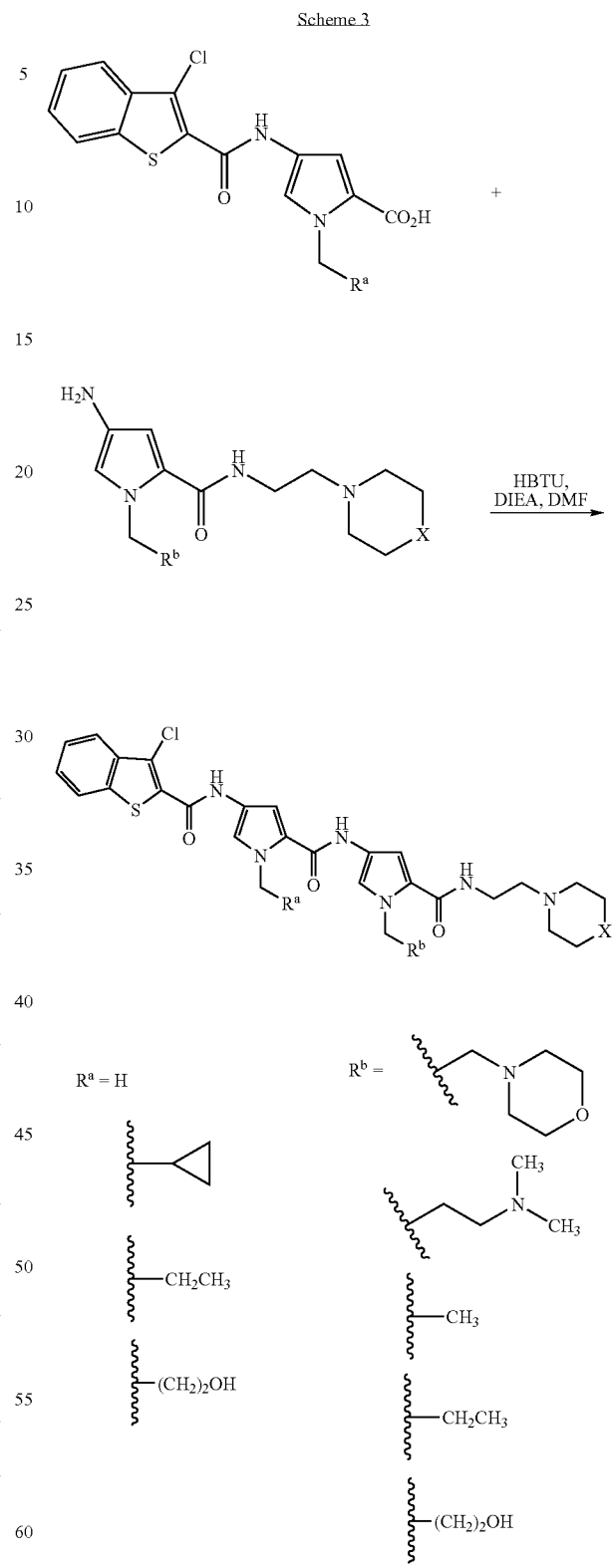

Synthesis of compound Ib-39 ($R^1$=$CH_2CH_3$, $R^2$=$CH_2CH_2OH$, X=$CH_2$). A mixture of the carboxylic acid prepared in Example B ($R^1$=CH$_2$CH$_3$, 60 mg, 1.1 equiv.) and HBTU (60 mg) in NMP (1 mL) and DEA (0.2 mL) was stirred for 1 h at 37° C. and added to a solution of the pyrrole amine prepared in Example A ($R^2$=CH$_2$CH$_2$OH, X=CH$_2$) in NMP (1 mL) and DIEA (0.2 mL). The reaction mixture was stirred was stirred at 37° C. for 16 h, diluted with AcOH (2 mL) and H$_2$O (5 mL), and washed with Et$_2$O (3×). Preparative HPLC of the aqueous layer gave compound Ib-39. The $^1$H-NMR spectrum and mass spectrum were in agreement with the structure of compound Ib-39.

EXAMPLE D

In this example, intermediates synthesized per Examples A and B (variation b) are coupled to provide compounds of this invention. The synthetic scheme is summarized in Scheme 3a and a detailed representative procedure is provided with specific reference to compound Ib-33.

The convergent synthetic strategy depicted in Examples A through D is easily applicable for the preparation of additional compounds of this invention beyond the ones specifically illustrated, including those having pyrrole carboxamide units in which the pyrrole unit is unsubstituted, such as Ib-22, Ib-23, Ib-25, Ib-27, Ib-30, Ib-35, or Ib-37 or in which one or more five member heterocycles is other than pyrrole, as in compounds Ib-21 and Ib-27. The synthesis and use of intermediates having unsubstituted ("desmethyl") pyrrole moieties is described in Bremer et al., *Bioorg. Med. Chem.*, 2000, 8, 1947–1955, incorporated herein by reference. The synthesis and use of intermediates having 5-member heterocycles other than pyrrole is described in, inter alia, Dervan, U.S. Pat. No. 6,090,947 (2000); Dervan, WO 98/49142 (1998); Beria et al., U.S. Pat. No. 5,753,629 (1998); and Boger et al., *J. Am. Chem. Soc.* 2000, 122, 6382–6394; the disclosures of which are incorporated herein by reference.

Scheme 3a

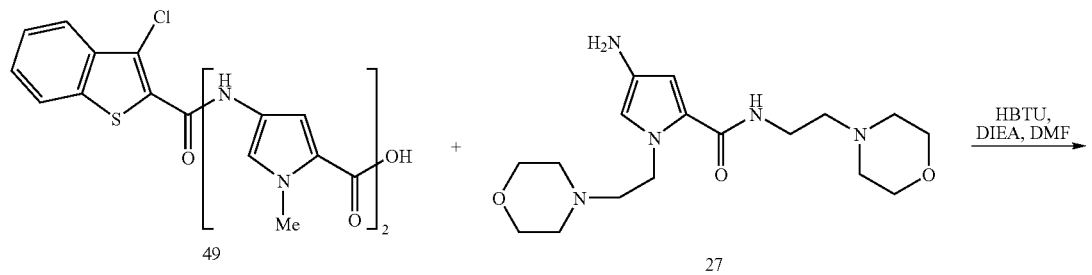

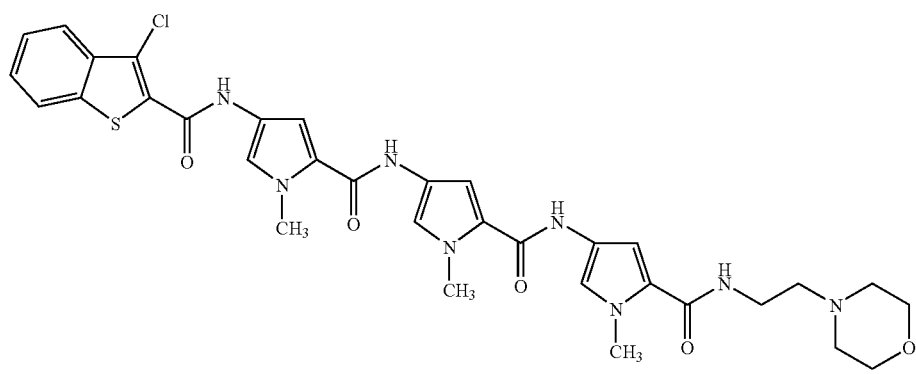

Ib-33

Synthesis of Compound Ib-33. A mixture of the trimeric carboxylic acid 49 (119 mg, 1.2 equiv.) and HBTU (93.8 mg, 1.14 equiv.) in NMP (ca. 1 mL) and DIEA (ca. 0.2 mL) was stirred at 40° C. for 1 h and added to a soln. of the pyrrole amine 27 (100 mg, 1.0 equiv.) in NMP (ca. 1 mL) and DIEA (ca. 0.2 mL). The solution was stirred at 40° C. for 16 h, diluted with 50% aqueous AcOH and washed with Et$_2$O (1×). Preparative HPLC of the aqueous phase gave compound Ib-33. The $^1$H-NMR spectrum and mass spectrum were in agreement with the structure of compound Ib-33.

EXAMPLE E

This example illustrates the synthesis of compounds having a benzothiophene moiety coupled to a sequence of two or three N-methylpyrrole carboxamide moieties, with specific reference to compound Ib-1. Those skilled in the art will understand that other compounds having such a structural motif, such as Ib-2 through Ib-20, can be analogously synthesized, mutatis mutandis. The procedure is summarized in Scheme 4.

Scheme 4

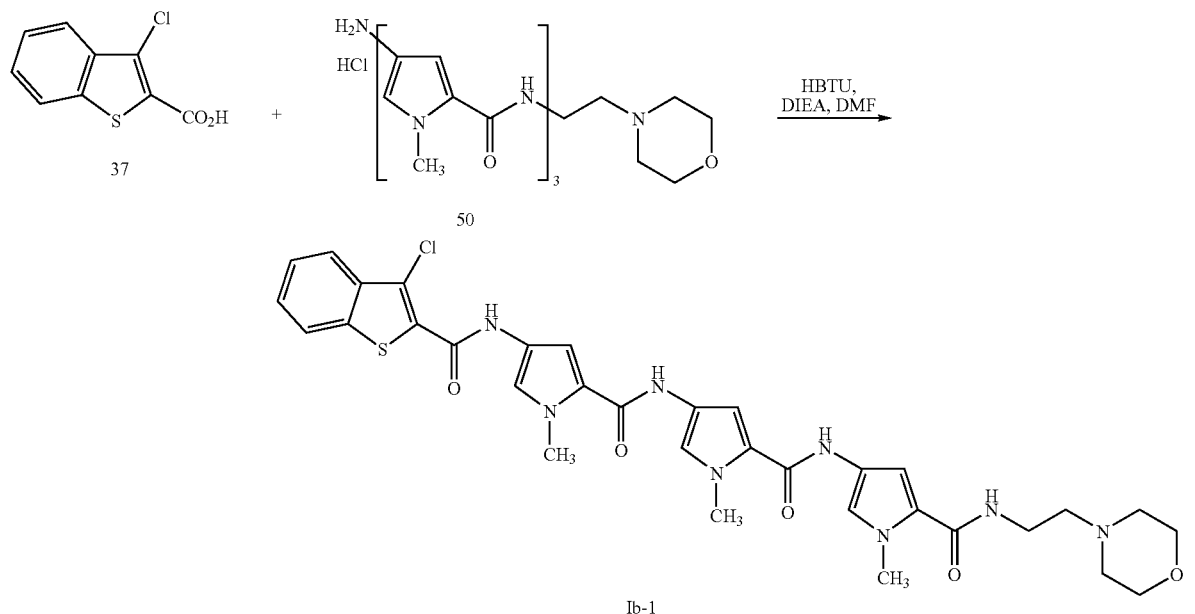

Synthesis of Compound Ib-1. A mixture of 3-chlorobenzothiophene-2-carboxylic acid 37 (36 mg, 1.2 equiv.), HBTU (61 mg, 1.14 equiv.) in DMF (1 mL) and DIEA (0.2 mL) was stirred for 30 min at 37° C., added to the trimeric amine 50 (70 mg, 1 equiv.; Baird et al., U.S. Provisional Application No. 60/286,454, filed Apr. 26, 2001, incorporated herein by reference) and stirred for 23 h at 37° C. The mixture was diluted with 50% aqueous AcOH and washed with Et$_2$O (1×). Preparative HPLC of the aqueous layer gave Ib-1. The $^1$H-NMR spectrum and mass spectrum were in agreement with the structure of Ib-1.

Alternatively compound Ib-1 can be synthesized by the HBTU mediated coupling acid 49 with amine 129, which is synthesized as follows:

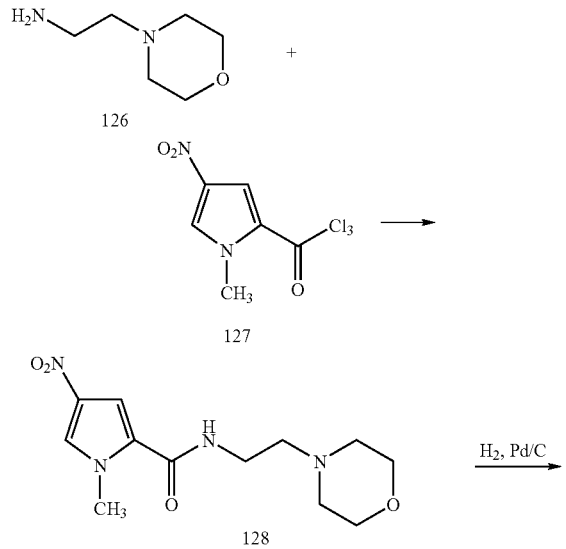

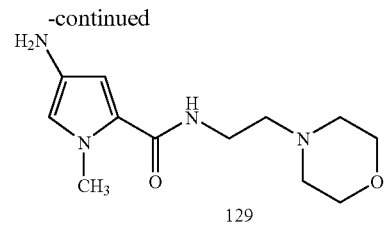

Nitropyrrole 128. 1-methyl-2-trichloroacetyl-4-nitropyrrole 127 (135.2 g, 0.498 mole) was added into the solution of 4-(2-aminoethyl)morpholine 126 (65 g, 0.499 mole) in THF (600 mL) in a 1 L three-necked round-bottomed flask while stirring at room temperature. The reaction was exothermic, and the reaction temperature reached 50° C. in 3 min. The reaction was completed in 2 hr according to TLC [CH$_2$Cl$_2$:MeOH (v/v)=9:1]. The reaction mixture was concentrated in vacuo to remove THF and triturated with ether (300 mL). The resulting solid was filtered, washed with ether, and dried to afford nitropyrrole 128 as a light yellow solid (136 g, 0.482 mole, 96.5% yield).

Crude nitropyrrole 128 (68 g) was dissolved in 400 ml dry EtOAc under reflux. The resulting solution was then cooled to 0° C. for 4 h. After filtration and drying under high vacuum, pure nitropyrrole 128 (62 g, 88% yield) was obtained.

Amine 129. Pd/C (10%) (2.5 g) was added into a solution of nitropyrrole 128 (50 g, 0.177 mole, recrystallized per above) in THF (500 mL) in a 2 L autoclave under N$_2$. The autoclave was then de-gassed under vacuum. H$_2$ was passed into the autoclave and the reaction proceeded at 125 psi at room temperature. After stirring for 2 h, the reaction was completed according to TLC (Toluene:EtOAc=7:3 (v/v), R$_{f(NO2Py1208)}$=0.85). The reaction mixture was filtered through a Celite cake, diluted with anhydrous ether (2 L). HCl (gas) was passed through the reaction mixture to precipitate out the amine 129 hydrochloride. Pure product (48 g, 0.166 mole, 94% yield) was obtained after filtration and washing with diethyl ether (3×50 mL) and drying under vacuum.

Compound Ib-1. DIEA (46 g, 0.36 mole) was added into a solution of acid 49 (68.4 g, 0.15 mole) and HBTU (64 g, 0.16 mole) in DMF (1000 mL) in a 2 L round bottom flask while stirring at room temperature. The reaction mixture was stirred at 45° C. for 30 min. Then amine 128 hydrochloride (52 g, 0.18 mole, 1.2 eq) was added into the reaction mixture and stirred at 50° C. After 15 h, the reaction was completed according to TLC. The reaction mixture was cooled to room temperature and poured into 1.5 L ice water under vigorous stirring. The resulting precipitate was filtered, and recrystalization from MeOH gave compound Ib-1 (57 g, 0.082 mole, 55% yield).

EXAMPLE F

This example illustrates the synthesis of compounds having an unsubstituted ("desmethyl") pyrrole carboxamide unit, such as compounds Ib-26, Ib-47 to Ib-49, and Ib-52. Scheme 4 summarizes the procedure with particular reference to compound Ib-48, it being understood that analogous compounds can be made, mutatis mutandis.

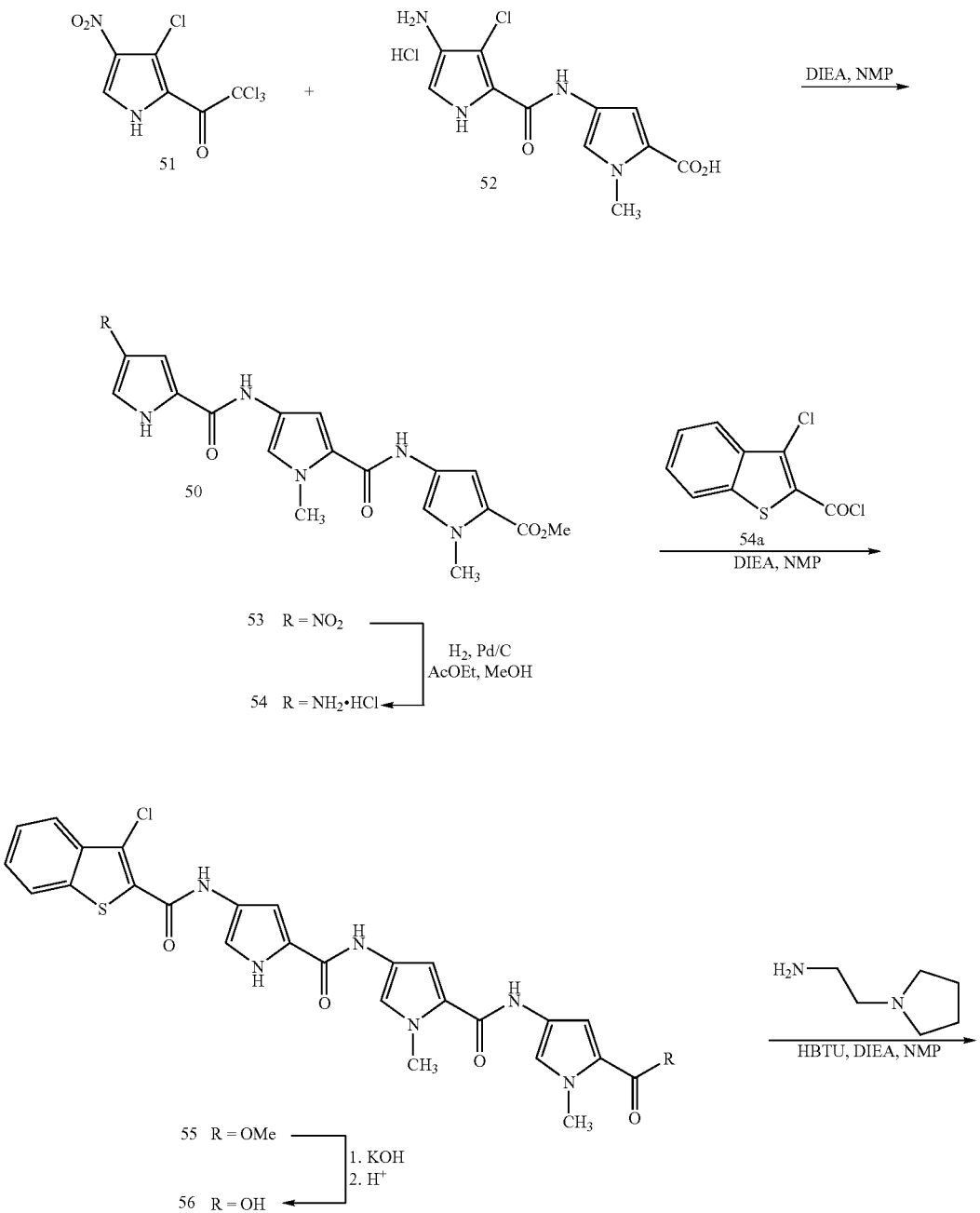

-continued

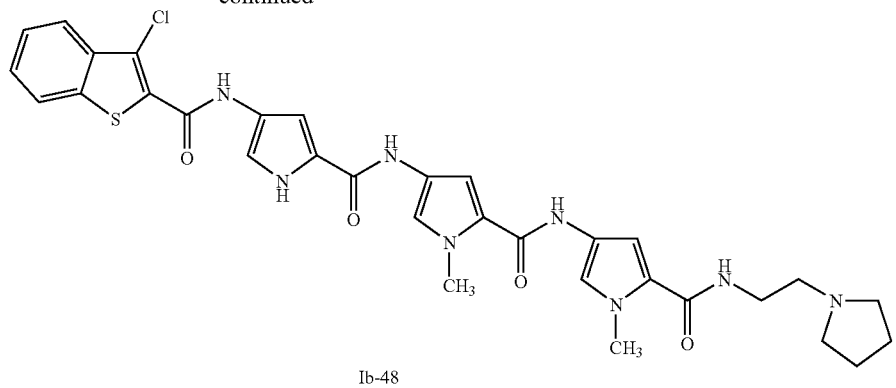

Ib-48

Synthesis of the trimer 53. A mixture of the ketone 51 (6.00 g, 1 equiv.) and the amine 52 (7.27 g, 1 equiv.) in NMP (50 mL) and DIEA (9.5 mL) was stirred for 2 h at RT and added dropwise to ice water (800 mL). The resulting solids were collected by filtration and dried in vacuo to give the trimer 53 (9.40 g, 97%). The $^1$H-NMR spectrum was in agreement with the structure of 53.

Synthesis of the trimeric amine 54. A suspension of 53 (1.19 g, 1 equiv.) and 10% Pd—C (0.2 g) in AcOEt (30 mL) and MeOH (30 mL) was stirred at RT under $H_2$ atmosphere (100 psi) for 16 h. The mixture was filtered through Celite and evaporated. The residue was diluted with MeOH, treated with HCl (g) and diluted with $Et_2O$ (ca. 200 mL). The resulting precipitates were collected by filtration and dried to give 54 (1.0 g, 83%). The $^1$H-NMR spectrum was in agreement with the structure of 54.

Synthesis of the tetramer 55. A mixture of the amine 54 (2.90 g, 1.0 equiv.) and the acid chloride 54a (1.75 g, 1.1 equiv.) in NMP (10 mL) and DIEA 3 mL) was stirred for 2½ h at RT (exothermic) and added dropwise to ca. 10% $K_2CO_3$ in ice water (400 mL). The resulting solids were collected by filtration, dried and directly converted further to 56.

Synthesis of the tetrameric acid 56. The crude tetramer 55 was dissolved in EtOH (40 mL), treated with 1M aqueous KOH (40 mL), and stirred for 6 h at 60° C. The mixture was diluted with $H_2O$ and washed with $Et_2O$ (1×). The aqueous layer was acidified to pH≈2 and the resulting precipitate collected by filtration and dried to give 56 (2.2 g, 57% over two steps). The $^1$H-NMR spectrum was in agreement with the structure of 56.

Synthesis of compound Ib-48. A mixture of the tetramer 56 (80 mg, 1 equiv.) and HBTU (60 mg, 1.1 equiv.) in NMP (1 mL) and DIEA (0.1 mL) was stirred at 37° C. for 30 min, treated with 1-(2-aminoethyl)pyrrolidine (ca. 0.1 mL) and stirred at 37° C. for ca. 12 h. The crude product was diluted with 50% aqueous AcOH and washed with $Et_2O$ (1×). Preparative HPLC of the aqueous layer gave compound Ib-48. The $^1$H-NMR spectrum and mass spectrum were in agreement with the structure of compound Ib-48.

EXAMPLE G

Compounds in the series Id, having a hairpin turn, can be synthesized using solid phase techniques, in which a benzothiophene containing intermediate such as compound 37, 47, or 49 is coupled to a resin bound intermediate containing moieties $M^1$, $M^2$, and/or $M^3$. Then, a desired amine is used to cleave the resin bound precursor off the resin. Dervan et al., U.S. Pat. No. 6,090,947 (2000) and Baird et al., U.S. Provisional Patent Application No. 60/286,454, filed Apr. 26, 2001, the disclosures of which are incorporated by reference, disclose solid phase techniques that can be adapted to synthesize compounds of this invention, mutatis mutandis.

EXAMPLE H

Compounds in the series Ie also can be made by solid phase techniques, again adapting the techniques disclosed in the aforementioned Dervan '947 patent and Baird '454 application, mutatis mutandis.

EXAMPLE I

Compounds in which $-Z(R^2)_n$ is

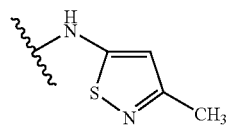

such as compounds Ib-53 and Ib-54, are made by coupling commercially available 5-amino-3-methylisothiazole with the complementary carboxylic acid intermediate. The coupling preferably is effected with O-(7-azabenzotriazol-1-yl)-N,N,N',N'-tetramethyluronium hexafluorophosphate ("HATU"), which produces a more activated ester than HBTU, compensating for the lesser reactivity of the aromatic amine group compared to an aliphatic amine group. Also, it may be desirable to run the coupling reaction at a more elevated temperature.

EXAMPLE J

Preparation of Substituted Benzothiophene Building Blocks.

a)

Preparation of 5,6-methylenedioxy and 5,6-dihydroxy benzothiophenes compounds. Treatment of 3,4-methylenedioxy cinnamic acid 100 with $SOCl_2$ gave the 3-chlorobenzothiophene 101. This acid chloride was used for the preparation of compounds such as Ib-20d to Ib-20i, Ib-20l to Ib-20r, Ib-59 to Ib-71, Ib-73, and Ib-74, respectively (standard coupling of 101 to the corresponding intermediates bearing an amino group). Compound 101 was also converted to the carboxylic acid 104 (by hydrogenolytic dechlorination followed by saponification) and to the dihydroxy derivative 105 (by Lewis-acid catalyzed deprotection). These carboxylate derivatives can be coupled to intermediates bearing an amino group using a standard amide bond formation protocol (HBTU or BOPCl activation or via the corresponding acid chloride); e.g., 104 was converted to its acid chloride (by refluxing in $SOCl_2$ for 5 min) and further converted to compounds Ib-20w and Ib-20i. The experimental procedures for the preparation of these building blocks are described below.

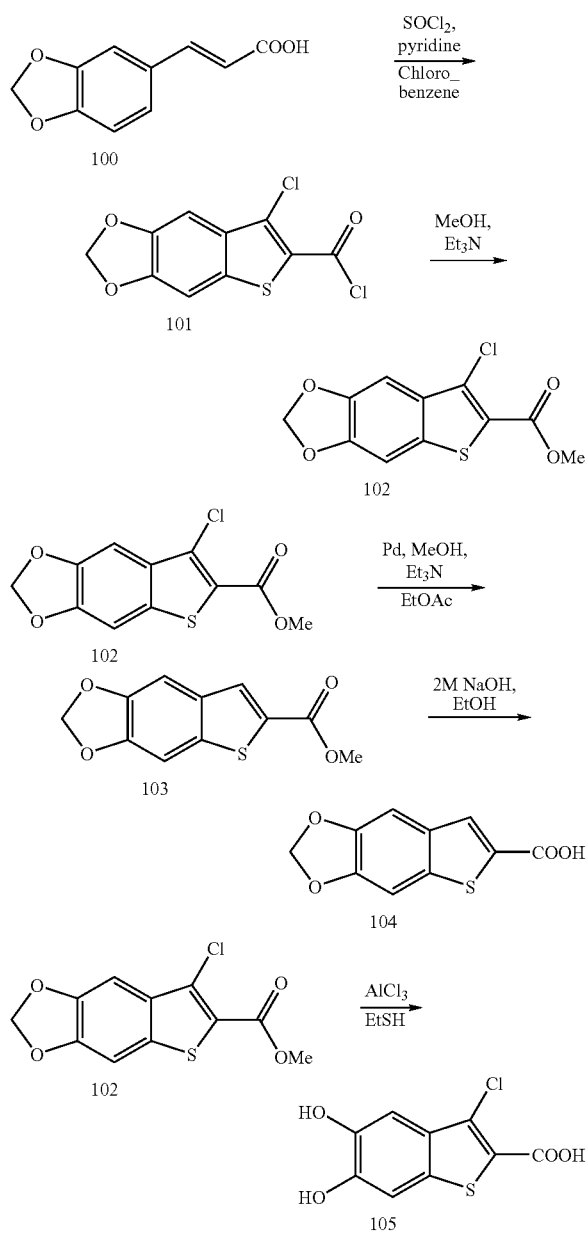

Synthesis of acid chloride 101. A mixture of the cinnamic acid 100 (15.58 g, 1.0 equiv.), $SOCl_2$ (30 ml, 5.0 equiv.) and pyridine (0.7 ml, 0.1 equiv.) in chlorobenzene (80 ml) was refluxed for 3 days under $N_2$, cooled to RT and treated with AcOEt (30 ml). The resulting yellow solids collected by filtration, washed with cold AcOEt (2×, each 20 ml) and dried to give the acid chloride 101 (ca. 15 g, 67%). The $^1$H-NMR spectrum of the crude product indicated that the material was pure enough for the next conversion.

Synthesis of methyl ester 102. A solution of the crude acid chloride 101 (ca. 15 g) in MeOH (150 ml) and $Et_3N$ (10 ml) was refluxed for 30 min and cooled to 0° C. The resulting precipitate was collected by filtration and washed with $H_2O$ (3×, each 30 ml), MeOH (2×, each 30 ml) and $Et_2O$ (20 ml) and dried to give the methyl ester 102 quantitatively (95% purity according to $^1$H-NMR spectrum).

Dechlorination to ester 103. A suspension of compound 102 (2.0 g) and Pd (black, 400 mg) in MeOH/EtOAc (2:1, 300 ml) and $Et_3N$ (2 ml) was stirred at ca. 80° C. for 3 days and filtered through Celite. Solvent evaporation gave compound 103 quantitatively, which was used without further purification.

Synthesis of acid 104. A mixture of the ester 103 (1.0 g) in EtOH (15 ml) and 2 M aqueous NaOH (15 ml) was stirred at 60° C. for 2 h and poured into acidic ice-water (400 ml, ca. 3 M HCl). The resulting precipitate was collected by filtration, washed with $H_2O$ and dried to give the carboxylic acid 104 as yellow solids (0.82 g, 87%). The product was characterized by $^1$H-NMR.

Synthesis of acid 105. A mixture of the ester 102 (1.50 g) and $AlCl_3$ (2.90 g, 4 equiv.) in EtSH (20 ml) was stirred at RT for 2 h, treated with 1M HCl ice water (100 mL) and extracted with AcOEt (3×100 ml). The combined organic layers were washed with 1M aqueous HCl, $H_2O$ and brine, dried over anhydrous $Na_2SO_4$ and evaporated to give compound 105 (1.2 g, 89%). The product was characterized by $^1$H-NMR and used without further purification.

EXAMPLE K

Synthesis of other substituted benzothiophene compounds. Apart from compound 101, other benzothiophene-2-carboxylate derivatives bearing substituents at positions 4 to 7 can be conveniently prepared by treating the corresponding cinnamic acid derivative with thionyl chloride (synthetic procedure analogous to the preparation of 101). The resulting acid chloride can be purified by crystallization. In some cases, conversion to the corresponding methyl ester followed by purification by flash chromatography may be preferred. The acid chlorides 106 and 107, shown in the following Scheme, are specific examples of such benzothiophene building blocks. They have been used for the preparation of antibacterial molecules (e.g., Ib-20c from 106, Ib-20j from 107, standard amide bond formation protocol). The products of these cyclization reactions may be further derivatized; for instance, the nitro compound 107 was converted to the dimethylamine 108 by esterification, hydrogenation to the amine, dimethylation and saponification. 108 served as a building block for the preparation of Ib-20k.

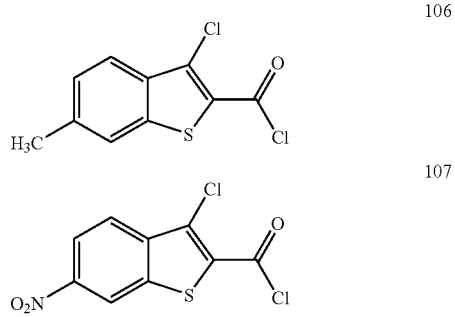

-continued

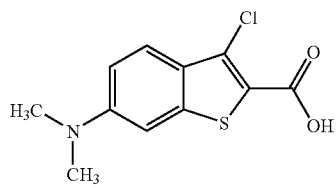

108

EXAMPLE L

Pegylated pyrrole building blocks. A 4-nitro-pyrrole bearing a carboxylic ester or an amide function at position 2 can be alkylated at the ring nitrogen. The experimental details for the preparation of the pegylated pyrrole dimer 115 are described below. This dimer was used for the preparation of compound Ib-61 (standard coupling of the acid chloride 101 and 115). Other nitro pyrroles, for instance the ethyl 4-nitro-pyrrole-2-carboxylate 1, can be substituted (pegylated) analogously.

Synthesis of nitro compound 112. A mixture of the trichloroketone 110 (11.32 g, 1.0 equiv.), the amine 111 (15.00 g, 1.0 equiv.) in DMF (80 ml) and DIEA (20 ml) was stirred at RT for 20 h and poured into $H_2O$ (ca. 600 ml) and sat. aqueous $K_2CO_3$. The solution was extracted with AcOEt (6×) and the organic layers dried ($MgSO_4$) and evaporated to give 112 as yellow solids (structure confirmed by $^1$H-NMR).

Synthesis of nitro compound 114. A mixture of the dimer 112 (1.00 g, 1.0 equiv.), the chloride 113 (3.67 g, 2.5 equiv.), NaI (576 mg, 1.5 equiv.), and $K_2CO_3$ (884 mg, 2.5 equiv.) in DMF (ca. 30 ml) was stirred at 65° C. for 48 h, diluted with AcOEt (150 ml), and washed with sat. aqueous $K_2CO_3$ and $H_2O$ (2×). The combined organic layers were dried ($MgSO_4$) and evaporated. Flash chromatography of the resulting oil ($CH_2Cl_2$: 0→15% MeOH) gave 114 as a yellow solid (785 mg, 57%, structure confirmed by $^1$H-NMR and MS).

Synthesis of amine 115. A suspension of 114 (780 mg) and 10% Pd—C (200 mg) in AcOEt (36 ml) and MeOH (4 ml) was stirred at RT under $H_2$ (1 atm) for 22 h and filtered through Celite. The filtrate was treated with HCl (g) for ca.

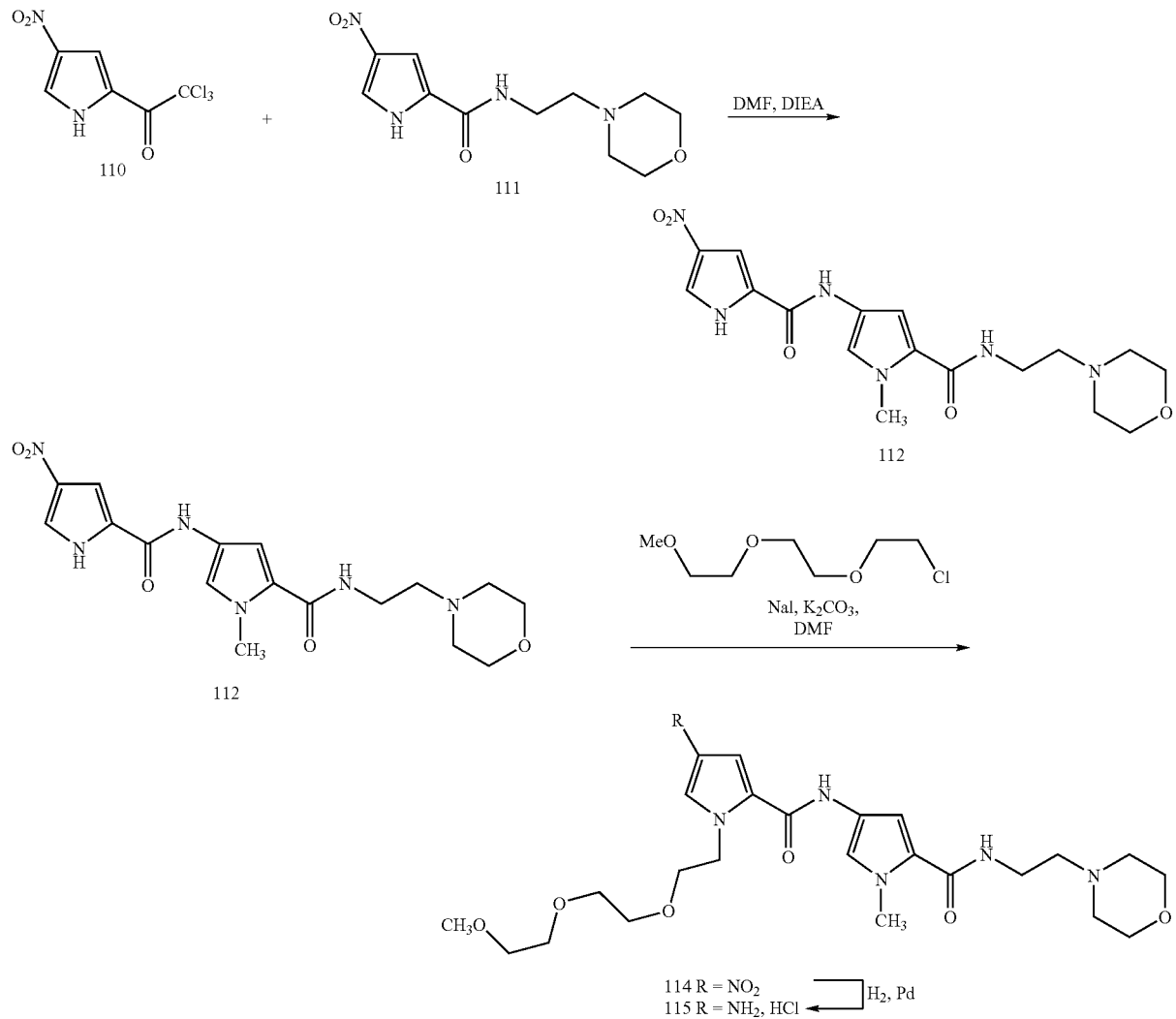

Scheme 7

15 seconds and evaporated to give 115 as a tan solid (804 mg, structure confirmed by ¹H-NMR and MS).

EXAMPLE M 3,5-disubstituted isothiazoles can be used as internal building blocks for antibacterial molecules as exemplified by compound Ib-56 (shown in Scheme 8 below). Importantly, the free amino group of isothiazole derivatives such as 117 is rather unreactive: thus, amide bond formations at such sites were performed using more reactive activated carboxylic acids such as acid chlorides and/or elevated reaction temperatures and prolonged reaction times.

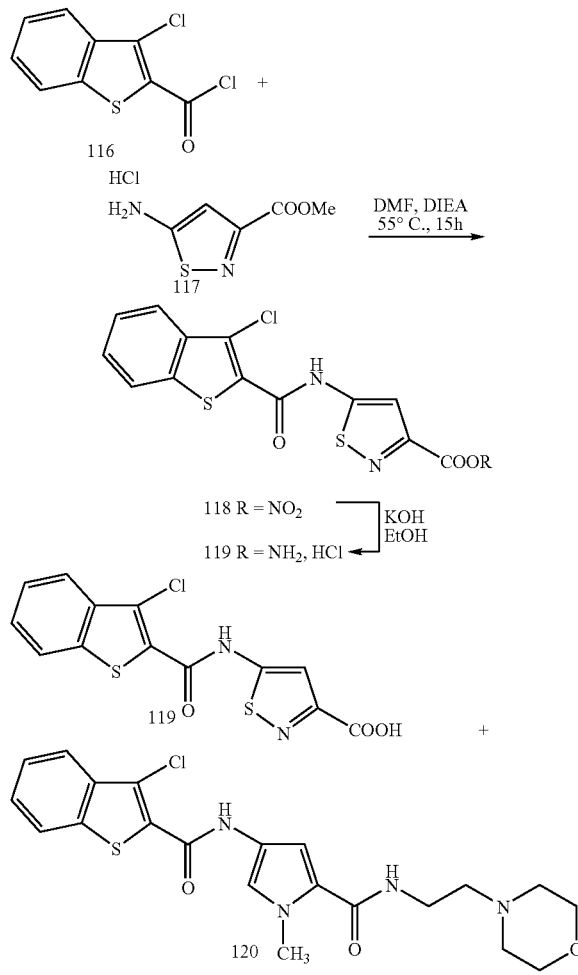

Scheme 8

EXAMPLE N

In vitro biological activity data were collected for a variety of microorganisms, including *Bacillus cereus* (ATCC 11778), *Staphylococcus aureus* (ATCC 27660 (a methicillin resistant strain (MRSA), ATCC 33591 and ATCC 43300); ATCC 13709, a methicillin sensitive strain (MSSA)); *Streptococcus pneumoniae* (ATCC 51422, a penicillin resistant strain (PRSP)), *Enterococcus faecium* (ATCC 51559, a vancomycin resistant strain (VRE)), and *Staphylococcus epidermidis* (ATCC 700586, a methycillin resistant strain (MRSE)). Additionally, antifungal activity data were collected for *Candida albicans* (ATCC 38247). Minimal inhibition concentrations (MIC's) were determined using the National Committee for Clinical Laboratory Standards (NCCLS) broth microdilution assay in microtiter plates, as set forth in: (1) the guidelines of the National Committee for Clinical Laboratory Standards (NCCLS) Document M7-A4 (NCCLS, 1997); (2) the guidelines of the National Committee for Clinical Laboratory Standards (NCCLS) Document M11-A4 (NCCLS, 1997); and (3) the guidelines and reference method of the National Committee for Clinical Laboratory Standards (NCCLS) Document M27-T (NCCLS, 1995). For antifungal essays, the method recommended in Murray, P R., 1995 *Manual of Clinical Microbiology* (ASM Press, Washington, D.C.), was employed. The results are presented in Table A below, which is keyed as follows:

Organisms tested against:

A = *B. cereus* ATCC 11778　　B = *E.faecium* ATCC 51559
C = *S. aureus* ATCC 13709　　D = *S. aureus* ATCC 27660
E = *S. aureus* ATCC 33591　　F = *S. aureus* ATCC 43300
G = *S. epidermidis* ATCC 700586　　H = *S. pneumoniae* ATCC 51422

Activity:

+++ = MIC ≤ 4　　++ = MIC between 4 and 12
+ = MIC from 12 to 32, inclusive　　ND Not determined
>32 = preliminary data indicates MIC greater than 32

TABLE A

Antibacterial activity

Organism (Minimum Inhibitory Concentration (MIC), µg/mL)

| Compound | A | B | C | D | E | F | G | H |
|---|---|---|---|---|---|---|---|---|
| Ib-1 | +++ | +++ | +++ | +++ | +++ | +++ | +++ | +++ |
| Ib-2 | +++ | ND | ND | ND | ND | ND | ND | ND |
| Ib-3 | +++ | +++ | ND | ++ | +++ | ++ | +++ | +++ |
| Ib-4 | +++ | +++ | +++ | +++ | +++ | +++ | +++ | +++ |
| Ib-5 | +++ | ND | ND | ND | ND | ND | ND | ND |
| Ib-6 | +++ | +++ | +++ | +++ | +++ | +++ | +++ | +++ |
| Ib-7 | +++ | ND | ND | ND | ND | ND | ND | ND |
| Ib-8 | + | +++ | ++ | ++ | +++ | +++ | +++ | +++ |
| Ib-9 | +++ | +++ | +++ | +++ | +++ | +++ | +++ | +++ |
| Ib-10 | +++ | +++ | +++ | +++ | +++ | +++ | +++ | +++ |
| Ib-12 | +++ | +++ | +++ | +++ | +++ | ND | +++ | +++ |
| Ib-13 | +++ | ND | +++ | +++ | ND | ND | ND | ND |
| Ib-14 | +++ | ND | +++ | +++ | ND | ND | ND | ND |
| Ib-15 | +++ | ND | +++ | +++ | ND | ND | ND | ND |
| Ib-16 | ++ | ND | +++ | +++ | ND | ND | ND | ND |
| Ib-17 | +++ | + | +++ | +++ | +++ | ND | +++ | |
| Ib-18 | +++ | +++ | +++ | +++ | +++ | +++ | +++ | +++ |
| Ib-19 | >32 | ND | +++ | +++ | ND | ND | ND | ND |
| Ib-20 | +++ | ND | +++ | +++ | ND | ND | ND | ND |
| Ib-20a | +++ | ND | +++ | +++ | ND | ND | ND | ND |
| Ib-20b | +++ | ND | +++ | +++ | +++ | ND | ND | ND |
| Ib-20c | +++ | ND | +++ | +++ | ND | ND | ND | ND |
| Ib-20d | +++ | +++ | +++ | +++ | +++ | ND | +++ | +++ |
| Ib-20e | +++ | +++ | +++ | +++ | +++ | ND | +++ | +++ |
| Ib-20f | +++ | ND | +++ | +++ | +++ | ND | ND | ND |
| Ib-20g | +++ | ND | +++ | +++ | +++ | ND | +++ | +++ |
| Ib-20h | +++ | ND | +++ | +++ | +++ | ND | ND | ND |
| Ib-20i | +++ | ND | +++ | +++ | ND | ND | ND | ND |
| Ib-20j | +++ | ND | +++ | +++ | +++ | ND | ND | ND |
| Ib-20k | >32 | ND | +++ | +++ | ND | ND | ND | ND |
| Ib-20l | +++ | ND | +++ | +++ | ND | ND | ND | ND |
| Ib-20m | +++ | +++ | +++ | +++ | +++ | ND | +++ | +++ |
| Ib-20n | +++ | ND | +++ | +++ | ND | ND | ND | ND |
| Ib-20o | +++ | +++ | +++ | +++ | +++ | ND | +++ | +++ |
| Ib-20p | +++ | +++ | +++ | +++ | +++ | ND | +++ | +++ |

TABLE A-continued

Antibacterial activity

Organism (Minimum Inhibitory Concentration (MIC), µg/mL)

| Compound | A | B | C | D | E | F | G | H |
|---|---|---|---|---|---|---|---|---|
| Ib-20q | >32 | ND | +++ | +++ | +++ | ND | ND | ND |
| Ib-20r | +++ | +++ | +++ | +++ | +++ | ND | +++ | +++ |
| Ib-20s | +++ | ND | +++ | +++ | +++ | ND | ND | ND |
| Ib-20t | +++ | ND | +++ | +++ | +++ | ND | ND | ND |
| Ib-20u | +++ | ND | +++ | +++ | +++ | ND | ND | ND |
| Ib-20v | +++ | ND | +++ | +++ | +++ | ND | ND | ND |
| Ib-20w | +++ | ND | +++ | +++ | +++ | ND | ND | ND |
| Ib-20x | +++ | ND | +++ | +++ | +++ | ND | ND | ND |
| Ib-21 | >32 | ND | ND | ND | ND | ND | ND | ND |
| Ib-22 | + | ND | ND | ND | ND | ND | ND | ND |
| Ib-23 | ++ | ND | ND | ND | ND | ND | ND | ND |
| Ib-24 | +++ | ND | ND | ND | ND | ND | ND | ND |
| Ib-25 | +++ | ND | ND | ND | ND | ND | ND | ND |
| Ib-26 | +++ | +++ | +++ | +++ | ND | +++ | +++ | +++ |
| Ib-27 | +++ | ND | +++ | +++ | ND | ND | ND | ND |
| Ib-28 | +++ | + | +++ | +++ | +++ | ND | +++ | +++ |
| Ib-29 | +++ | +++ | +++ | +++ | +++ | ND | +++ | +++ |
| Ib-30 | +++ | ND | +++ | +++ | ND | ND | ND | ND |
| Ib-31 | +++ | +++ | +++ | +++ | +++ | ND | +++ | +++ |
| Ib-32 | +++ | +++ | +++ | +++ | +++ | ND | +++ | +++ |
| Ib-33 | +++ | +++ | +++ | +++ | +++ | ND | +++ | +++ |
| Ib-34 | +++ | +++ | +++ | +++ | +++ | ND | +++ | +++ |
| Ib-35 | +++ | +++ | +++ | +++ | +++ | ND | +++ | +++ |
| Ib-36 | +++ | ND | +++ | +++ | +++ | ND | ND | ND |
| Ib-37 | +++ | ND | +++ | +++ | ND | ND | ND | ND |
| Ib-38 | +++ | +++ | +++ | +++ | +++ | +++ | +++ | +++ |
| Ib-39 | +++ | +++ | ++ | +++ | ND | ND | ND | ND |
| Ib-40 | +++ | +++ | +++ | +++ | +++ | ND | +++ | +++ |
| Ib-41 | +++ | ND | + | +++ | ND | ND | ND | ND |
| Ib-42 | +++ | +++ | +++ | +++ | ++ | ND | + | +++ |
| Ib-43 | +++ | +++ | +++ | +++ | +++ | ND | +++ | +++ |
| Ib-44 | +++ | +++ | +++ | +++ | +++ | ND | +++ | +++ |
| Ib-45 | +++ | +++ | +++ | +++ | +++ | ND | +++ | +++ |
| Ib-46 | +++ | ND | +++ | +++ | ND | ND | ND | ND |
| Ib-47 | +++ | + | +++ | +++ | +++ | ND | +++ | +++ |
| Ib-48 | +++ | ++ | +++ | +++ | +++ | ND | +++ | +++ |
| Ib-49 | +++ | ND | +++ | ++ | ND | ND | ND | ND |
| Ib-50 | +++ | ND | +++ | +++ | ND | ND | ND | ND |
| Ib-51 | +++ | ND | +++ | +++ | ND | ND | ND | ND |
| Ib-52 | +++ | ND | +++ | ++ | ND | ND | ND | ND |
| Ib-53 | ++ | ND | ++ | + | ND | ND | ND | ND |
| Ib-54 | ++ | ND | + | + | ND | ND | ND | ND |
| Ib-55 | +++ | +++ | +++ | +++ | +++ | ND | +++ | +++ |
| Ib-56 | >32 | +++ | +++ | +++ | +++ | ND | +++ | +++ |
| Ib-57 | +++ | ND | +++ | +++ | +++ | ND | ND | ND |
| Ib-58 | +++ | ND | +++ | +++ | +++ | ND | ND | ND |
| Ib-59 | +++ | +++ | +++ | +++ | +++ | ND | +++ | +++ |
| Ib-60 | +++ | +++ | +++ | +++ | +++ | ND | +++ | +++ |
| Ib-61 | +++ | +++ | +++ | +++ | +++ | ND | +++ | +++ |
| Ib-62 | + | +++ | +++ | +++ | +++ | ND | +++ | +++ |
| Ib-63 | +++ | +++ | +++ | +++ | +++ | ND | +++ | +++ |
| Ib-64 | +++ | +++ | +++ | +++ | +++ | ND | +++ | +++ |
| Ib-65 | +++ | +++ | +++ | +++ | +++ | ND | +++ | +++ |
| Ib-66 | +++ | +++ | +++ | +++ | +++ | ND | +++ | +++ |
| Ib-67 | +++ | +++ | +++ | +++ | +++ | ND | +++ | +++ |
| Ib-68 | +++ | +++ | +++ | +++ | +++ | ND | +++ | +++ |
| Ib-69 | >32 | +++ | +++ | +++ | +++ | ND | +++ | +++ |
| Ib-70 | +++ | +++ | +++ | +++ | +++ | ND | +++ | +++ |
| Ib-71 | +++ | +++ | +++ | +++ | +++ | ND | +++ | +++ |
| Ib-72 | +++ | +++ | +++ | +++ | +++ | ND | +++ | + |
| Ib-73 | +++ | ND | +++ | +++ | +++ | ND | ND | ND |
| Ib-74 | +++ | +++ | +++ | +++ | +++ | ND | +++ | +++ |
| Ib-75 | +++ | +++ | +++ | +++ | +++ | ND | +++ | +++ |
| Ib-76 | +++ | +++ | +++ | +++ | +++ | ND | +++ | +++ |
| Ib-77 | +++ | +++ | +++ | +++ | +++ | ND | +++ | +++ |
| Ib-78 | +++ | ND | +++ | +++ | +++ | ND | ND | ND |
| Id-1 | >32 | ND | ND | ND | ND | ND | ND | ND |
| Id-4 | >32 | ND | + | + | ND | ND | ND | ND |
| Ie-1 | +++ | ND | ND | ND | ND | ND | ND | ND |
| Ie-2 | +++ | ND | ND | ND | ND | ND | ND | ND |
| Ie-3 | +++ | ND | ND | ND | ND | ND | ND | ND |
| Ie-4 | +++ | ND | +++ | +++ | +++ | ND | ND | ND |

The data of Table A shows that compounds of this invention are particularly active against Gram-positive bacteria.

Additionally, some of the compounds of this invention possess anti-fungal activity, as evidenced by their activity against *Candida albicans* (ATCC 38247). The data is presented in Table B. (MIC values are keyed in the same manner as in Table 3.)

TABLE B

Activity against *Candida albicans* (ATCC 38247)

| Compound Ref. | (MIC), µ/mL |
|---|---|
| Ib-08 | ++ |
| Ib-44 | +++ |
| Ib-45 | + |
| Ib-47 | +++ |
| Ib-48 | +++ |
| Ib-50 | ++ |
| Ib-51 | +++ |
| Ib-02 | +++ |
| Ib-27 | + |
| Ib-13 | ++ |
| Ib-29 | + |
| Ib-32 | +++ |
| Ib-19 | + |
| Ib-39 | + |
| Ib-43 | + |

EXAMPLE O

This example demonstrates in vivo efficacy against infection by methycillin resistant *Staphylococcus aureus* ATCC 33591, using a murine neutropenic thigh model.

A *S. aureus* ATCC 33591 culture was grown to log phase overnight and diluted in phosphate buffered saline (pH 7.2) to an optical density of about 0.1 at 600 nm, giving an approximate concentration of $10^8$ cfu/mL. The suspension was diluted 1:100 in phosphate buffered saline (pH 7.2) for a final concentration of $10^6$ cfu/mL.

Outbred female CF1 mice (approx. 20 gram body weight) were rendered neutropenic by treatment with cyclophosphamide (200 mg/kg body weight, intraperitoneal injection) at 2 and 4 days prior to inoculation. Groups of 5 mice were inoculated with 0.05 mL of the bacteria (approx. $10^6$ cfu/mL) into the anterior thigh. Each group was treated intravenously two hours post infection with vehicle (phosphate buffered saline) or test compound. The mice were sacrificed at either 6 or 24 hrs after treatment and thighs were collected aseptically. Each thigh was weighed, placed into sterile saline, and homogenized. The tissue homogenates were diluted appropriately for plating on agar plates. Colony counts were recorded (cfu/gram) and compared to control groups. The data are presented in Table 4 below:

TABLE C

Murine Neutropenic Thigh Model

| Compound No. (Time) | Dose (mg/kg) | Colony Count (log cfu/gram) Compound | Vehicle |
|---|---|---|---|
| Ib-26 (6 hr) | 80 | 6.17 | 7.83 |
| Ib-47 (6 hr) | 50 | 6.11 | 8.01 |
| Ib-48 (6 hr) | 50 | 4.74 | 8.01 |
| Ib-50 (6 hr) | 50 | 7.97 | 8.67 |
| Ib-51 (6 br) | 50 | 7.04 | 8.27 |

In vivo efficacy was shown by a decrease in colony count (log cfu/gram of tissue) in the compound-treated animals when compared against the colony count in animals given only the vehicle.

EXAMPLE P

This example illustrates the DNA binding properties of compounds of this invention using a DNase I footprinting technique. Generally, the procedure described in Dervan, WO 98/50582 (1998), was followed.

Double stranded circular plasmids A and B were used to prepare double stranded DNA-binding probes containing the target sequences for the DNase I footprint titration experiments.

Plasmid A was prepared by hybridizing two sets of 5'-phosphorylated complementary oligonucleotides, the first set being 5'-CTAGATGCCGCTAAGTACTATGCCGCTAACTACTATGCCGCTAAT
TACTATGCCGC-3' (SEQ ID NO:3)
and 5'-CATAGTAATTAGCGGCATAGTAGTTAGCGGCATAGTACTTAGCGG
CAT-3' (SEQ ID NO:4);
and
the second set being 5'-TAAATACTATGCCGCTAACTAGTATGCCGCTATGCA-3'
(SEQ ID NO:5)
and

5'-TAGCGGCATACTAGTTAGCGGCATAGTATTTAGCGG-3'
(SEQ ID NO:6), and ligating the resulting duplexes to the large pUC19 XbaI/PstI restriction fragment.

Plasmid B was the plasmid pTrc99a, obtained from Amersham Pharmacia Biotech, Inc.

The 3'-P32 end-labeled EcoRI/PvuII fragments from each plasmid were prepared by digesting the plasmids with EcoRI and PvuII with simultaneous fill-in using Sequenase v. 2.0, [alpha-P32]-deoxyadenosine-5'-triphosphate, and [alpha-P32]-thymidine-5'-triphosphate, and isolating the cloned fragments by nondenaturing gel electrophoresis. A and G sequencing reactions were carried out as described (See Maxam and Gilbert, *Methods Enzymol.*, 1980, 65, 499–560; Iverson and Dervan, *Methods Enzymol.*, 1987, 15, 7823–7830; Sambrook et al., 1989, *Molecular Cloning*, 2$^{nd}$ ed., Cold Spring Harbor Laboratory Press: Cold Spring Harbor, N.Y.) Standard methods were used for all DNA manipulations (Sambrook et al., ibid.)

The 310 base pair dsDNA restriction fragment (SEQ ID NO:1) of Plasmid A contained a target sequences ACTACT. The 352 base pair dsDNA restriction fragment (SEQ ID NO:2) of Plasmid B contained target sequences GACAATTAATCA (SEQ ID NO:7) and AATTAATCAT (SEQ ID NO:8). These fragments were used for quantitative DNase I footprinting experiments. The target sequences were selected for their identity with, or similarity to, promoter sites for bacterial genes.

Quantitative DNase I footprint titration experiments were carried out as described previously (Dervan, WO 98/50582, 1998) with the following changes. All reactions were carried out in a total volume of 400 μL, with compound stock solution or water added to 15,000 cpm radiolabeled restriction fragment affording final solution conditions of 10 mM Tris HCl, 10 mM KCl, 10 mM $MgCl_2$, 5 mM $CaCl_2$, pH 7.0 and 0.01 nM, 0.1 nM, 1.0 nM, 10.0 nM compound or no compound for reference lanes. The compounds were allowed to equilibrate at 22° C. for 16 h. Footprinting reactions were initiated with addition of 10 μL of a DNase I stock solution (at the appropriate concentration to give ~50% intact DNA) containing 1 mM DTT and allowed to proceed for 7 min at 22° C. The reactions were stopped, ethanol precipitated, resuspended in loading buffer, heat denatured, and placed on ice as described previously (Dervan WO 98/50582, 1998). The reaction products were separated on a precast 8% polyacrylamide denaturing sequencing Castaway gel with 32 preformed wells from Stratagene in 1× TBE at 2000 V. Gels were dried according to the manufacturer and exposed to a storage phosphor screen (Molecular Dynamics). Quantitation and data analysis were carried out as described in Dervan, WO 98/50582, 1998.

dsDNA binding results are provided in Table D:

TABLE D dsDNA Binding

| Compound | Target Sequence (SEQ ID NO:) | Dissociation Constant $K_d$ (nM) | Target Location (Fragment/Plasmid). |
|---|---|---|---|
| Ib-1 | AATTAATCAT (8) | 0.2 | 352 bp/B |
| Ib-26 | GACAATTAATCA (7) | 0.1 | 352 bp/B |
| Ib-32 | AATACT (—) | 50 | 310 bp/A |
| Ib-32 | AATTAATCAT (8) | 10 | 352 bp/B |
| Ic-3 | ATTACT (—) | 50 | 310 bp/A |
| Ic-3 | AATTAATCAT (8) | 5 | 352 bp/B |

The foregoing detailed description of the invention includes passages that are chiefly or exclusively concerned with particular parts or aspects of the invention. It is to be understood that this is for clarity and convenience, that a particular feature may be relevant in more than just the passage in which it is disclosed, and that the disclosure herein includes all the appropriate combinations of information found in the different passages. Similarly, although the various figures and descriptions herein relate to specific embodiments of the invention, it is to be understood that where a specific feature is disclosed in the context of a particular figure or embodiment, such feature can also be used, to the extent appropriate, in the context of another figure or embodiment, in combination with another feature, or in the invention in general.

Further, while the present invention has been particularly described in terms of certain preferred embodiments, the invention is not limited to such preferred embodiments. Rather, the scope of the invention is defined by the appended claims.

SEQ ID NOS:

SEQ ID NO:1 (310 bp EdoRI/PvuII restriction fragment from Plasmid A; only one strand shown) AATTCGAGCTCGGTACCCGGGGATCCTCTAGATGCCGCTAAGTACTATGCCGCTAACTACTATGCCGCTAATTACTATGCCGCTAAATACTATGCCGCTAACTAGTATGCCGCTATGCAGGCATGCAAGCTTGGCGTAATCATGGTCATAGCTGTTTCCTGTGTGAAATTGTTATCCGCTCACAATTCCACACAACATACGAGCCGGAAGCATAAAGTGTAAAGCCTGGGGTGCCTAATGAGTGAGCTAACTCACATTAATTGCGTTGCGCTCACTGCCCGCTTTCCAGTCGGGAAACCTGTCGTGCCAG SEQ ID NO:2 (352 bp EdoRI/PvuII restriction fragment from Plasmid B; only one strand shown) CTGGCACGACAGGTTTCCCGACTGGAAAGCGGGCAGTGAGCGCAACGCAATTAATGTGAGTTAGCGCGAATTGATCTGGTTGACAGCTTATCATCGACTGCACGGTGCACCAATGCTTCTGGCGTCAGGCAGCCATCGGAAGCTGTGGTATGGCTGTGCAGGTCGTAAATCACTGCATAATTCGTGTCGCTCAAGGCGCACTCCCGTTCTGGATAATGTTTTTTGCGCCGACATCATAACGGTTCTGGCAAATATTCTGAAATGAGCTGTTGACAATTAATCATCCGGCTCGTATAATGTGTGGAATTGTGAGCGGATAACAATTTCACACAGGAAACAGACCATGGAATT

---

What is claimed is:

1. A composition comprising a pharmaceutically acceptable excipient and a compound having the formula

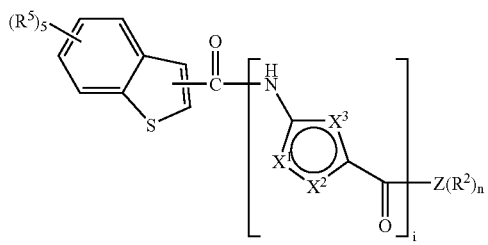

or the pharmaceutically acceptable salts thereof, wherein the subscript i is an integer of from 2 to 3, and in each ring having an $X^1$, $X^2$, and $X^3$, one of $X^1$, $X^2$, and $X^3$ is a ring vertex independently selected from the group consisting of —O—, —S—, and —$NR^2$—, and the other two of $X^1$, $X^2$, and $X^3$ are ring vertices independently selected from the group consisting of =N— and =$CR^1$—;

Z is O or N;

n is 1 if Z is O and 2 if Z is N;

each $R^1$ is independently H, F, Cl, Br, I, CN, OH, $NO_2$, $NH_2$, a substituted or unsubstituted ($C_1$–$C_{12}$)alkyl group, a substituted or unsubstituted ($C_1$–$C_{12}$)alkoxy group, or a substituted or unsubstituted ($C_1$–$C_{12}$)heteroalkyl group;

each $R^2$ is independently H, a substituted or unsubstituted ($C_1$–$C_{12}$)alkyl group, or a substituted or unsubstituted ($C_1$–$C_{12}$)heteroalkyl group;

or optionally, the group -Z($R^2$)$_n$ is selected from the group consisting of

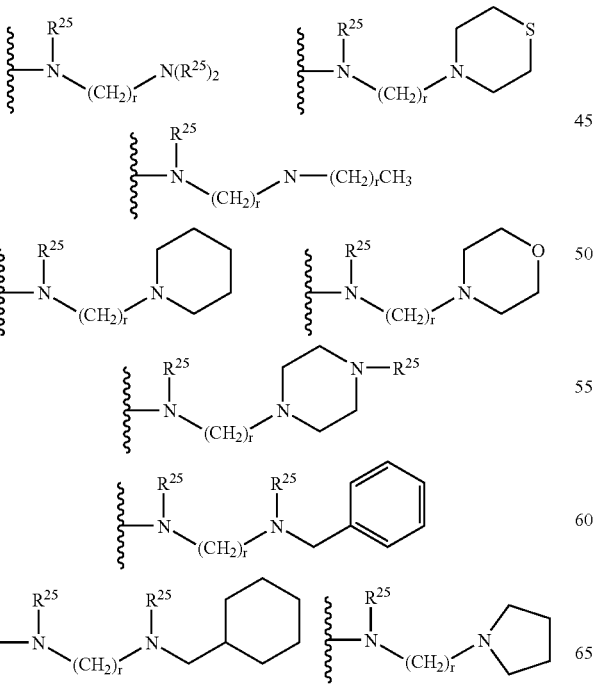

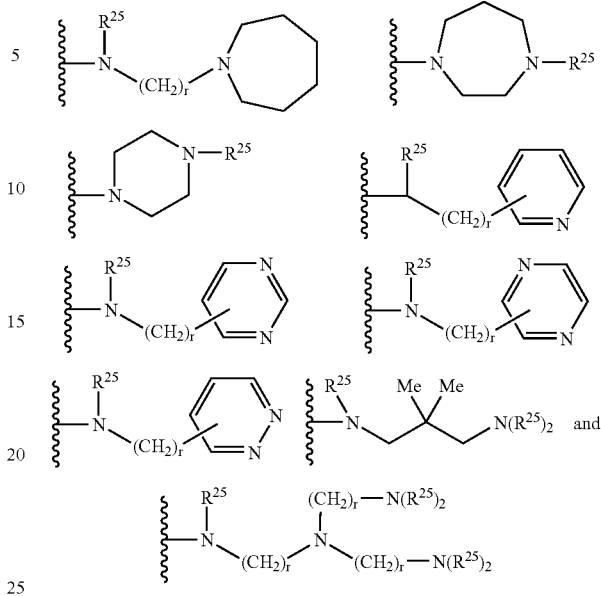

wherein each subscript r is independently an integer of from 2 to 8 and each $R^{25}$ is independently selected from the group consisting of H, $CH_3$, $CH_2CH_3$, $CH_2CH_2CH_3$ and $CH(CH_3)_2$; and each $R^5$ is independently H, F, Cl, Br, I, CN, OH, $NH_2$, $N(CH_3)_2$, a substituted or unsubstituted ($C_1$–$C_{12}$)alkyl group, a substituted or unsubstituted ($C_1$–$C_{12}$)alkoxy group, or a substituted or unsubstituted ($C_1$–$C_{12}$)heteroalkyl group; or optionally two adjacent $R^5$ groups are combined to form O—(CH($R^7$))$_t$—O, where t is 1 or 2 and each $R^7$ is independently H or a $C_1$–$C_6$ alkyl, alkenyl, alkynyl, or acyl group;

said compound having a basic group having a p$K_b$ of 12 or less or a quaternized nitrogen group.

2. A composition of claim 1, wherein the residue

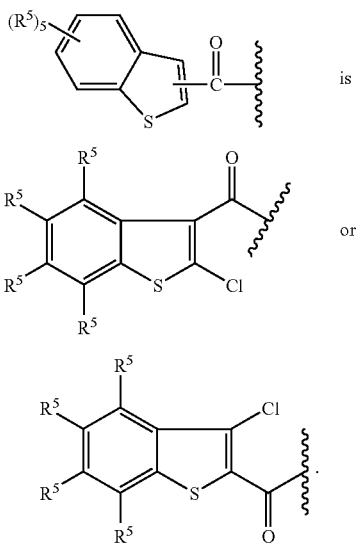

3. A composition of claim 2, wherein each $R^5$ is H.

4. A composition of claim 1, wherein the residue

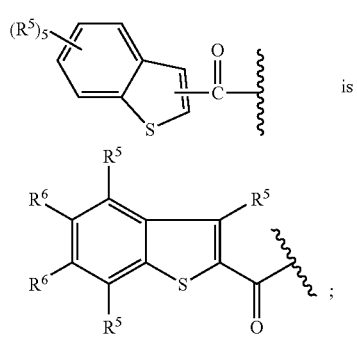

is

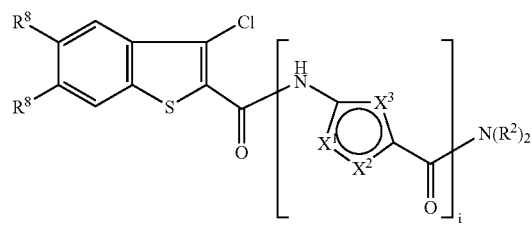

wherein the two $R^6$'s are both OH or $OCH_3$ or combine to form $O-(CH(R^7))_t-O$, where t is 1 or 2 and each $R^7$ is independently H or a $C_1-C_6$ alkyl, alkenyl, alkynyl, or acyl group.

5. A composition of claim 1, wherein said compound has the formula

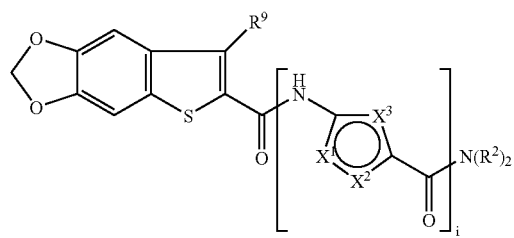

wherein one $R^8$ is H and the other $R^8$ is H, F, $CH_3$, $NO_2$, or $N(CH_3)_2$.

6. A composition of claim 1, wherein said compound has the formula

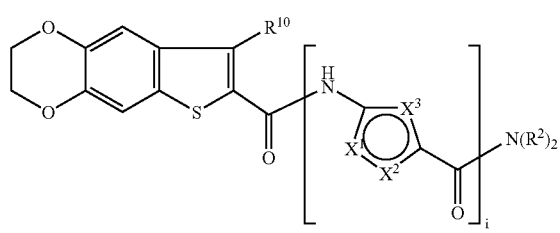

wherein $R^9$ is H or Cl.

7. A composition of claim 1, wherein said compound has the formula

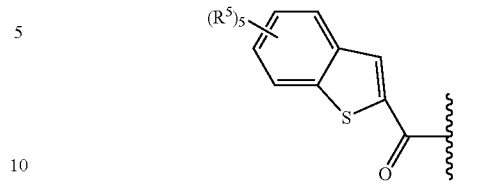

wherein $R^{10}$ is Cl or H.

8. A composition of claim 1, wherein the residue

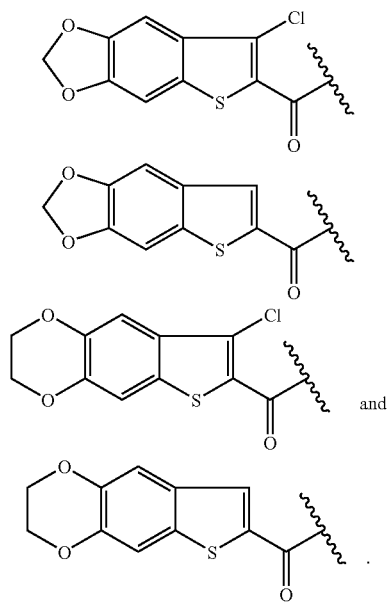

is selected from the group consisting of and

9. A composition of claim 1, wherein $-N(R^2)_2$ is a member selected from the group consisting of

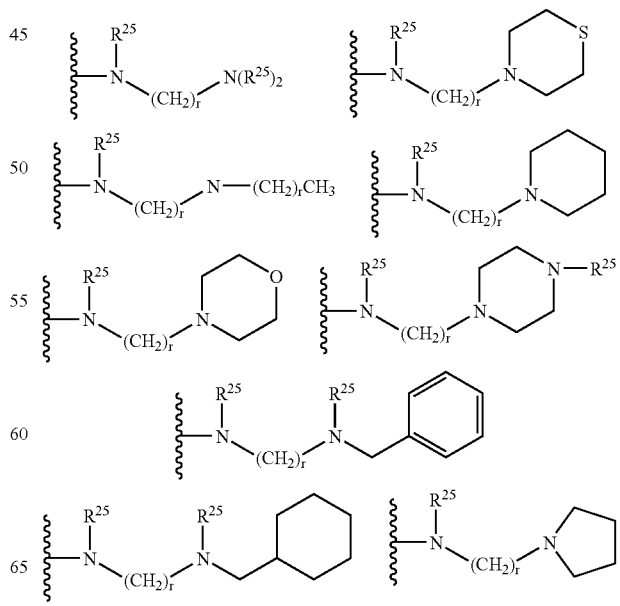

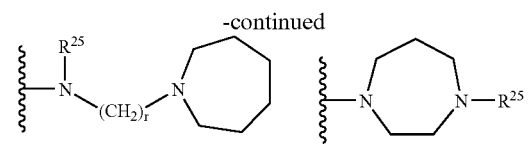
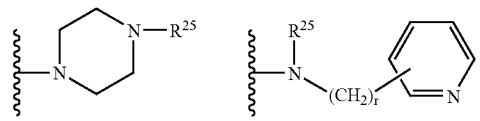
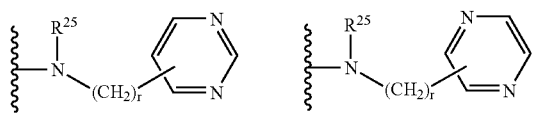
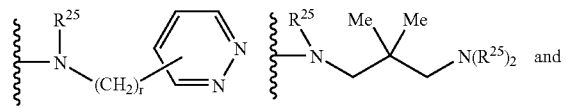
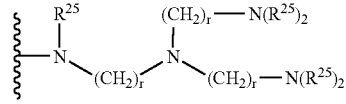

wherein each subscript r is independently an integer of from 2 to 8 and each $R^{25}$ is independently selected from the group consisting of H, $CH_3$, $CH_2CH_3$, $CH_2CH_2CH_3$ and $CH(CH_3)_2$.

10. A composition of claim 1, wherein each $X^1$ is =CH—; each $X^2$ is —$NR^2$—; and each $X^3$ is =CH—.

11. A composition of claim 1, wherein each $X^1$ is =CH—; each $X^2$ is —$NR^2$; each $X^3$ is =CH—; Z is —$N(R^2)_2$ and is a member selected from the group consisting of

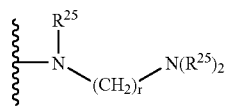
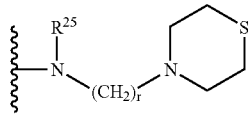
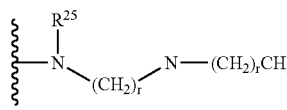
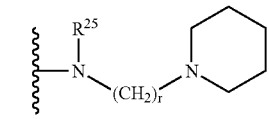
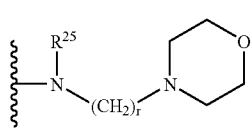
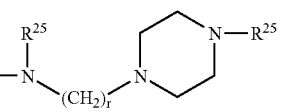
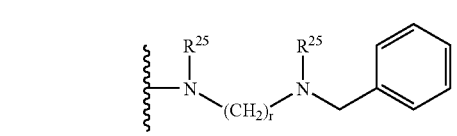
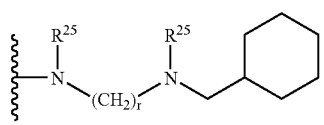

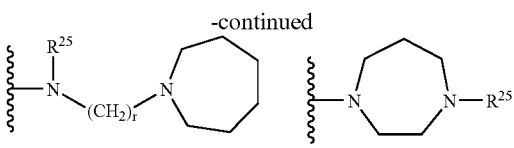
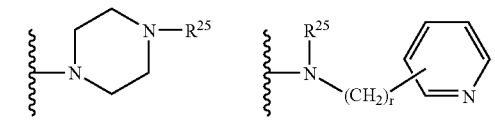
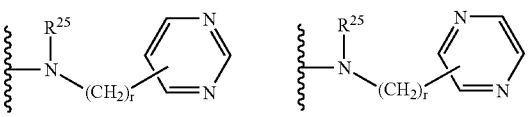
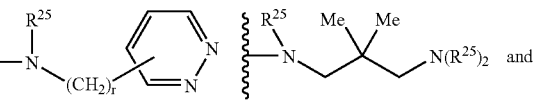

wherein each subscript r is independently an integer of from 2 to 8 and each $R^{25}$ is independently selected from the group consisting of H, $CH_3$, $CH_2CH_3$, $CH_2CH_2CH_3$ and $CH(CH_3)_2$.

12. A composition of claim 11, wherein the residue

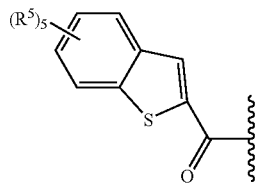

has the formula:

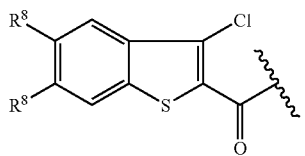

wherein one $R^8$ is H and the other $R^8$ is H, F, $CH_3$, $NO_2$, or $N(CH_3)_2$.

13. A composition of claim 12, wherein the residue

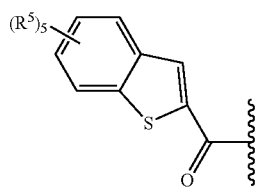

is selected from the group consisting of:
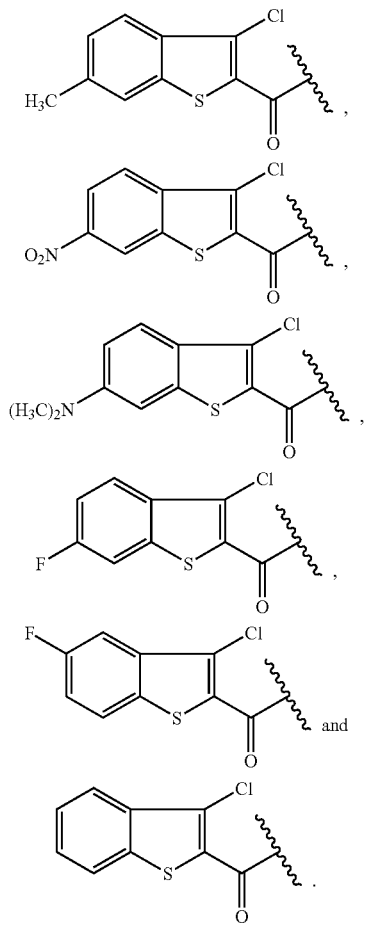
14. A composition of claim 13, wherein —N(R²)₂ is a member selected from the group consisting of
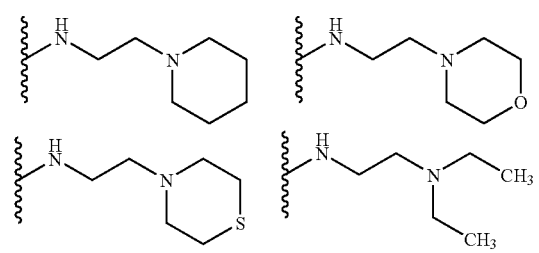
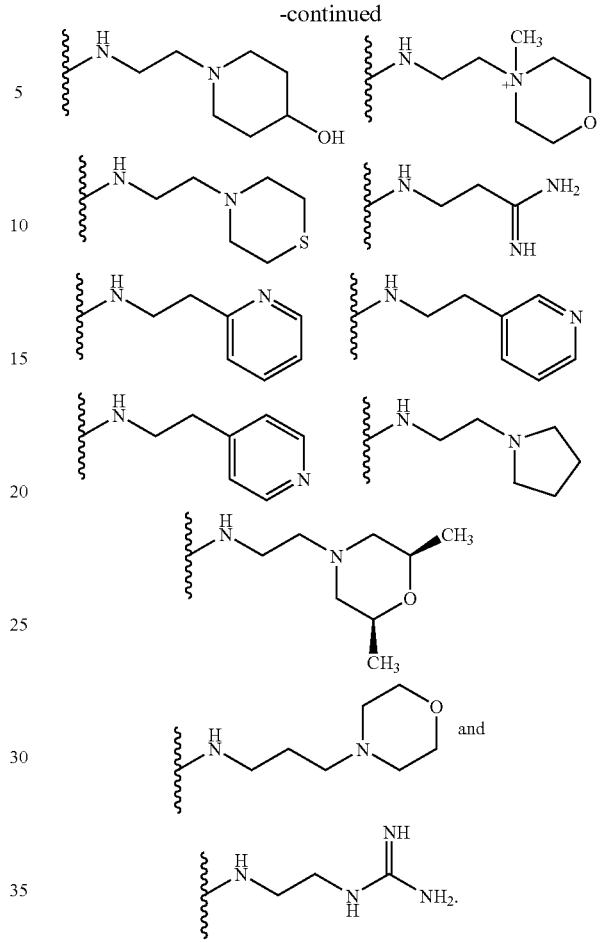
15. A composition of claim 14, wherein —N(R²)₂ is
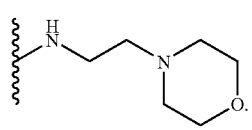
16. A method of treating a viral infection comprising administering to a subject in need of such treatment, a composition according to any of claims 1 to 10 and claims 11–15.
* * * * *

SEQUENCE LISTING

<160> NUMBER OF SEQ ID NOS: 8

<210> SEQ ID NO 1
<211> LENGTH: 310
<212> TYPE: DNA
<213> ORGANISM: Artificial Sequence
<220> FEATURE:
<223> OTHER INFORMATION: Description of Artificial Sequence:310 bp dsDNA
      EdoRI/PvuII restriction fragment from Plasmid A

<400> SEQUENCE: 1
aattcgagct cggtacccgg ggatcctcta gatgccgcta agtactatgc cgctaactac      60
tatgccgcta attactatgc cgctaaatac tatgccgcta actagtatgc cgctatgcag     120
gcatgcaagc ttggcgtaat catggtcata gctgtttcct gtgtgaaatt gttatccgct     180
cacaattcca cacaacatac gagccggaag cataaagtgt aaagcctggg gtgcctaatg     240
agtgagctaa ctcacattaa ttgcgttgcg ctcactgccc gctttccagt cgggaaacct     300
gtcgtgccag                                                            310

<210> SEQ ID NO 2
<211> LENGTH: 352
<212> TYPE: DNA
<213> ORGANISM: Artificial Sequence
<220> FEATURE:
<223> OTHER INFORMATION: Description of Artificial Sequence:352 bp dsDNA
      EdoRI/PvuII restriction fragment from Plasmid B

<400> SEQUENCE: 2
ctggcacgac aggtttcccg actggaaagc gggcagtgag cgcaacgcaa ttaatgtgag      60
ttagcgcgaa ttgatctggt tgacagcttt atcatcgact gcacggtgca ccaatgcttc    120
tggcgtcagg cagccatcgg aagctgtggt atggctgtgc aggtcgtaaa tcactgcata    180
attcgtgtcg ctcaaggcgc actcccgttc tggataatgt tttttgcgcc gacatcataa    240
cggttctggc aaatattctg aaatgagctg ttgacaatta atcatccggc tcgtataatg    300
tgtggaattg tgagcggata acaatttcac acaggaaaca gaccatggaa tt            352

<210> SEQ ID NO 3
<211> LENGTH: 56
<212> TYPE: DNA
<213> ORGANISM: Artificial Sequence
<220> FEATURE:
<223> OTHER INFORMATION: Description of Artificial
      Sequence:5'-phosphorylated complementary
      oligonucleotide for Plasmid A preparation -continued

```
<400> SEQUENCE: 3
ctagatgccg ctaagtacta tgccgctaac tactatgccg ctaattacta tgccgc         56

<210> SEQ ID NO 4
<211> LENGTH: 48
<212> TYPE: DNA
<213> ORGANISM: Artificial Sequence
<220> FEATURE:
<223> OTHER INFORMATION: Description of Artificial
      Sequence:5'-phosphorylated complementary
      oligonucleotide for Plasmid A preparation

<400> SEQUENCE: 4
catagtaatt agcggcatag tagttagcgg catagtactt agcggcat               48

<210> SEQ ID NO 5
<211> LENGTH: 36
<212> TYPE: DNA
<213> ORGANISM: Artificial Sequence
<220> FEATURE:
<223> OTHER INFORMATION: Description of Artificial
      Sequence:5'-phosphorylated complementary
      oligonucleotide for Plasmid A preparation

<400> SEQUENCE: 5
taaatactat gccgctaact agtatgccgc tatgca                           36

<210> SEQ ID NO 6
<211> LENGTH: 36
<212> TYPE: DNA
<213> ORGANISM: Artificial Sequence
<220> FEATURE:
<223> OTHER INFORMATION: Description of Artificial
      Sequence:5'-phosphorylated complementary
      oligonucleotide for Plasmid A preparation

<400> SEQUENCE: 6
tagcggcata ctagttagcg gcatagtatt tagcgg                           36

<210> SEQ ID NO 7
<211> LENGTH: 12
<212> TYPE: DNA
<213> ORGANISM: Artificial Sequence
<220> FEATURE:
<223> OTHER INFORMATION: Description of Artificial Sequence:Plasmid B
      target sequence

<400> SEQUENCE: 7
gacaattaat ca                                                     12

<210> SEQ ID NO 8
<211> LENGTH: 10
<212> TYPE: DNA
<213> ORGANISM: Artificial Sequence
<220> FEATURE:
<223> OTHER INFORMATION: Description of Artificial Sequence:Plasmid B
      target sequence

<400> SEQUENCE: 8
aattaatcat                                                        10
```